United States Patent
Zuckerman-Stark et al.

(10) Patent No.: US 11,571,137 B2
(45) Date of Patent: *Feb. 7, 2023

(54) ELECTRODE ARRAY FOR PHYSIOLOGICAL MONITORING AND DEVICE INCLUDING OR UTILIZING SAME

(71) Applicant: Medasense Biometrics Ltd., Ramat Gan (IL)

(72) Inventors: Galit Zuckerman-Stark, Tel Aviv (IL); Nir Ben-Israel, Tel Aviv (IL); Noam Racheli, Hadera (IL); Aviad Yeshaya, Holon (IL); Aviem Amossi, Hadera (IL)

(73) Assignee: MEDASENSE BIOMETRICS LTD., Ramat Gan (IL)

( * ) Notice: Subject to any disclaimer, the term of this patent is extended or adjusted under 35 U.S.C. 154(b) by 142 days.

This patent is subject to a terminal disclaimer.

(21) Appl. No.: 17/197,946

(22) Filed: Mar. 10, 2021

(65) Prior Publication Data
US 2021/0186359 A1   Jun. 24, 2021

Related U.S. Application Data

(63) Continuation of application No. 15/541,994, filed as application No. PCT/IL2016/050015 on Jan. 6, 2016, now Pat. No. 10,966,626.
(Continued)

(51) Int. Cl.
*A61B 5/0533* (2021.01)
*A61B 5/00* (2006.01)
(Continued)

(52) U.S. Cl.
CPC ........ *A61B 5/0533* (2013.01); *A61B 5/02055* (2013.01); *A61B 5/4824* (2013.01);
(Continued)

(58) Field of Classification Search
CPC . A61B 5/0533; A61B 5/02055; A61B 5/6826; A61B 5/0075; A61B 5/021; A61B 5/0816; A61B 2562/043
See application file for complete search history.

(56) References Cited

U.S. PATENT DOCUMENTS

| 4,183,986 A | 1/1980 | Blaetterlein |
| 4,425,921 A | 1/1984 | Fujisaki et al. |

(Continued)

FOREIGN PATENT DOCUMENTS

| CN | 1141585 A | 1/1997 |
| CN | 102475546 A | 5/2012 |

(Continued)

OTHER PUBLICATIONS

International Search Report for PCT/IL2016/050015 dated Apr. 21, 2016 (4 pages).
(Continued)

*Primary Examiner* — Jonathan T Kuo
(74) *Attorney, Agent, or Firm* — Greenberg Traurig, LLP

(57) ABSTRACT

Electrode array for monitoring of physiological parameters and devices including or utilizing same, the electrode array including an active electrode configured to provide an electrical signal and at least two inactive electrodes configured to collect the electrical signal transferred from the active electrode, wherein each of the at least two inactive electrodes are positioned at a different predetermined distance from the active electrode.

24 Claims, 8 Drawing Sheets

Related U.S. Application Data

(60) Provisional application No. 62/100,930, filed on Jan. 8, 2015.

(51) Int. Cl.
    *A61B 5/0205*     (2006.01)
    *A61B 5/0285*     (2006.01)
    *A61B 5/103*     (2006.01)
    *A61B 5/318*     (2021.01)
    *A61B 5/369*     (2021.01)
    *A61B 5/389*     (2021.01)
    *A61B 5/398*     (2021.01)
    *A61B 3/11*     (2006.01)
    *A61B 5/021*     (2006.01)
    *A61B 5/08*     (2006.01)

(52) U.S. Cl.
CPC .......... *A61B 5/6826* (2013.01); *A61B 5/6831* (2013.01); *A61B 5/6834* (2013.01); *A61B 3/112* (2013.01); *A61B 5/0075* (2013.01); *A61B 5/021* (2013.01); *A61B 5/0285* (2013.01); *A61B 5/0816* (2013.01); *A61B 5/103* (2013.01); *A61B 5/318* (2021.01); *A61B 5/369* (2021.01); *A61B 5/389* (2021.01); *A61B 5/398* (2021.01); *A61B 2560/0223* (2013.01); *A61B 2560/0252* (2013.01); *A61B 2562/0204* (2013.01); *A61B 2562/0219* (2013.01); *A61B 2562/043* (2013.01)

(56) References Cited

U.S. PATENT DOCUMENTS

| | | | |
|---|---|---|---|
| 6,181,808 | B1 | 1/2001 | Fukuzumi |
| 7,848,798 | B2 | 12/2010 | Martinsen et al. |
| 8,489,165 | B2 | 7/2013 | Segman |
| 8,781,565 | B2 | 7/2014 | Vartak et al. |
| 9,311,825 | B2 | 4/2016 | Lusted et al. |
| 9,439,599 | B2 | 9/2016 | Thompson et al. |
| 9,554,724 | B2 | 1/2017 | Schuessler |
| 9,830,781 | B2 | 11/2017 | Mirov et al. |
| 2004/0122336 | A1 | 6/2004 | Jang et al. |
| 2005/0113723 | A1 | 5/2005 | Ueyama et al. |
| 2005/0281441 | A1 | 12/2005 | Martinsen et al. |
| 2007/0043301 | A1 | 2/2007 | Martinsen et al. |
| 2007/0123756 | A1 | 5/2007 | Kitajima et al. |
| 2008/0001735 | A1 | 1/2008 | Tran |
| 2008/0214903 | A1 | 9/2008 | Orbach |
| 2009/0318779 | A1 | 12/2009 | Tran |
| 2010/0317936 | A1 | 12/2010 | Al-Ali et al. |
| 2013/0085367 | A1 | 4/2013 | Vartak et al. |
| 2013/0183646 | A1 | 7/2013 | Lusted et al. |
| 2014/0051941 | A1 | 2/2014 | Messerschmidt |
| 2014/0135602 | A1 | 5/2014 | Lemke |
| 2014/0228650 | A1 | 8/2014 | Ko et al. |
| 2014/0275845 | A1 | 9/2014 | Eagon et al. |
| 2015/0134264 | A1 | 5/2015 | Tansey |
| 2015/0157262 | A1 | 6/2015 | Schuessler |
| 2015/0327809 | A1 | 11/2015 | Tateda et al. |
| 2015/0364018 | A1 | 12/2015 | Mirov et al. |
| 2016/0007874 | A1 | 1/2016 | Ma et al. |
| 2017/0367614 | A1 | 12/2017 | Zuckerman-Stark et al. |

FOREIGN PATENT DOCUMENTS

| | | |
|---|---|---|
| EP | 0723417 B1 | 4/2003 |
| JP | 2000-310506 A | 11/2000 |
| JP | 2000-346609 A | 12/2000 |
| JP | 2005-013597 | 1/2005 |
| JP | 2014-514032 | 6/2014 |

OTHER PUBLICATIONS

Written Opinion of the International Searching Authority for PCT/IL2016/050015 dated Apr. 21, 2016 (5 pages).

Boucsein et al. (2012) Publication recommendations for electrodermal measurements: publication standards for EDA, Psych, No. 8, pp. 1017-1034, Aug. 2012.

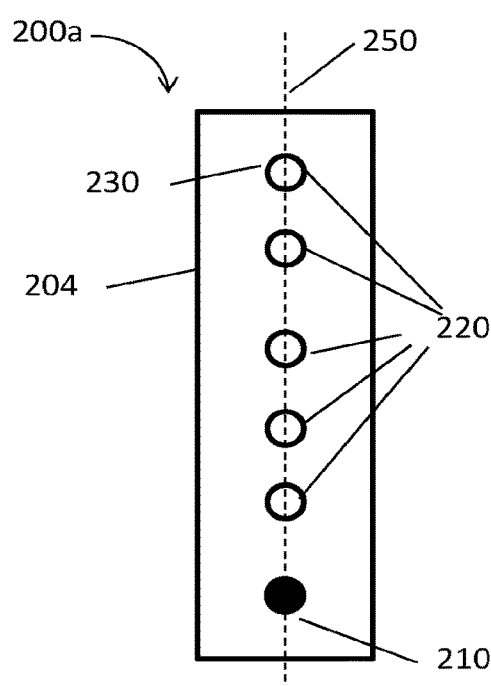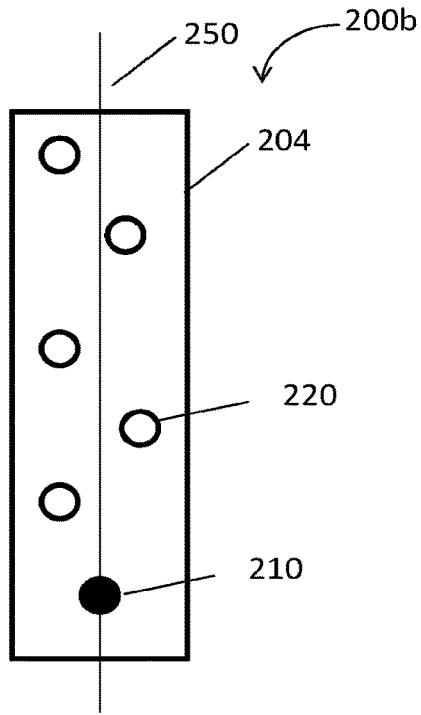
FIG. 2A  FIG. 2B
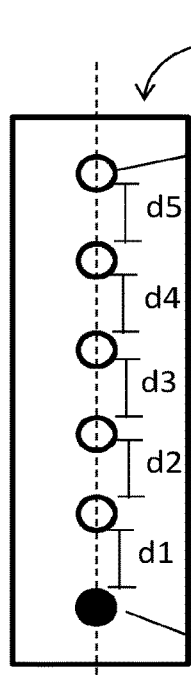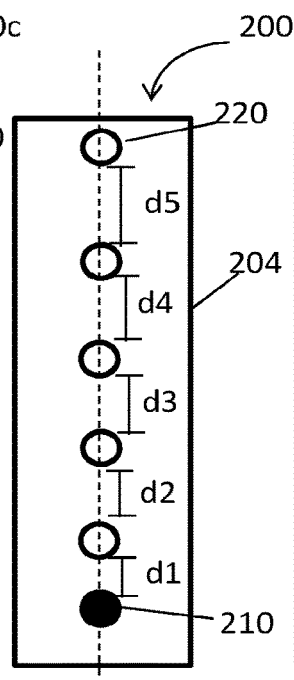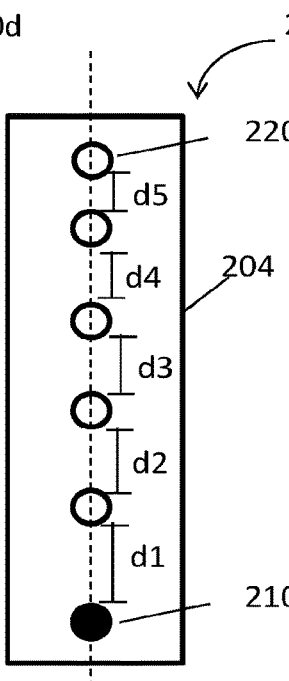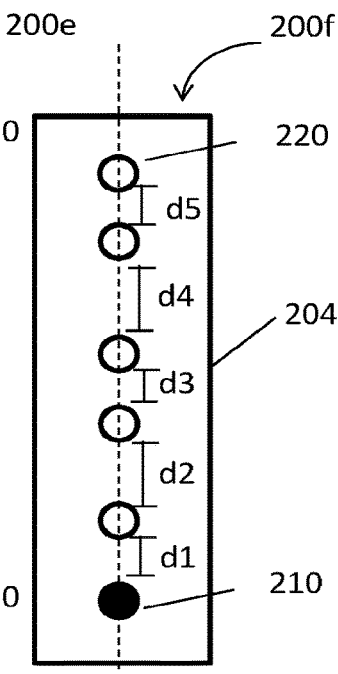
FIG. 2C  FIG. 2D  FIG. 2E  FIG. 2F

ELECTRODE ARRAY FOR PHYSIOLOGICAL MONITORING AND DEVICE INCLUDING OR UTILIZING SAME

RELATED APPLICATIONS

The present application is a continuation of U.S. application Ser. No. 15/541,994, filed on Jul. 6, 2017, which is a national phase filing under 35 USC 371 of International Application No. PCT/IL2016/050015, filed on Jan. 6, 2016, which claims priority from U.S. Provisional Application No. 62/100,930, filed on Jan. 8, 2015, the contents of which are incorporated herein in their entirety for all purposes.

TECHNICAL FIELD

The present disclosure relates generally to the field of monitoring of physiological signals and electrode arrays.

BACKGROUND

The sensation of pain is an extremely complex interaction of biological, cognitive, behavioral, cultural, and environmental factors. Yet the reaction of the body to an injury or noxious stimulus, e.g., an acute pain, is first and foremost a physiological response due to activation of the autonomic neural and hormonal pathways by a nociceptive stimulus. Nociception refers to the detection, transduction, and transmission of noxious stimuli that elicits an autonomic response even in an unconscious subject. Over the years, multiple studies have investigated nociception-related changes in different physiological parameters as the basis for objective assessment of the level of nociception during surgery.

The skin conductance response is the phenomenon that the skin momentarily becomes a better conductor of electricity when perspiration increases. A subject who has been exposed to a physiologically arousing situation will therefore display a sudden drop in resistance between two areas of the skin. A correlation between skin conductance and pain has also been demonstrated, in that skin conductance is elevated in response to nociception. Thus, measurement of changes in skin conductance is useful to provide an indication of pain levels.

Determination of skin conductance is typically based on measurements obtained from an active electrode configured to induce an electrical signal such as an electrical current, and an inactive electrode configured to collect the electrical signal. Typically, the active and inactive electrodes are positioned either on two fingers of the (same) hand or on the hand-palm.

The photo-plethysmographic waveform can provide information about parameters such as heart rate (HR), heart rate variability (HRV) and photo-plethysmographic amplitude (PPGA). These parameters are known as indicators of the autonomic function and nociceptive response.

While the above parameters may have a good correlation with the subject's pain level, confounders often cause a false detection. Integration of additional sensors, as accelerometer, thermometer and others, can provide the ability to reduce misdetection and increase the specificity for the subject's pain level.

SUMMARY

Aspects of the disclosure, in some embodiments thereof, relate to galvanic skin resistance (GSR) electrode arrays and devices including and/or utilizing same.

Generally, GSR measuring systems are based on measurements obtained from two electrodes, namely an active electrode and an inactive electrode or from three electrodes, including a combination of active and inactive electrodes, which typically are positioned either on two fingers of the (same) hand, on the hand-palm or on the foot in the case of neonates. The distance between the active and inactive electrodes influences the GSR measurements. As the distance between the active and inactive electrodes is enlarged, the resistance to current flow between the electrodes increases, but the sensitivity to changes in the measurements are increased. Oppositely, as the distance between the active and inactive electrodes is reduced, the resistance to current flow between the electrodes is also reduced, but the sensitivity to changes in the measurements is impaired. Furthermore, differences in skin dryness between individuals also influence the GSR readings in that subjects with dry skin have lower skin conductivity than subjects whose skin is damp. In fact, subjects with dry skin may have a conductivity so low that the changes in GSR measurements that are related to physiological arousal (e.g. pain) are difficult to obtain whereas others have a conductivity so high that the signal obtained is saturated, and changes in the conductivity of the skin go undetected.

Advantageously, the GSR electrode array enables compensation for inter person differences in skin dryness and/or in skin conductance properties. The compensation for inter person skin dryness differences is accomplished in that the GSR electrode array, disclosed herein, includes a scaffold having an active electrode and a plurality of inactive electrodes disposed thereon. The electrodes are positioned on the scaffold such that each inactive electrode is located at a different predetermined distance from the active electrode. On the one hand this enables customizing the distance between the active electrode and the inactive electrode to accommodate differences in skin dryness and/or the length of the finger, while on the other hand, given the distance between the electrodes is known, its impact on the measured value can be taken into consideration when determining changes in the conductivity of the skin.

In addition, the GSR electrode array, disclosed herein, may include additional elements configured to ensure optimal GSR readings and/or to provide an indication to the analyzer as to which of the inactive electrodes is utilized for the GSR measurements and thereby as to the distance between the specific inactive electrode and the active electrode.

For example, the array may include one or more resistors. The resistor may enable shifting of the electrical signal to be compatible with an applied measurement range. A resistor may, for example, be connected to each or some of the plurality of inactive electrodes so as to harmonize their measurement scale.

Furthermore, incorporation of one or more resistors and/or diodes may provide at least a partial defibrillation protection to a monitor, a sensor or any other equipment connected to the array and to an electricity supply. Advantageously, implementing the defibrillation protection inside the array may enable use of the GSR electrode array on systems that have no defibrillation protection.

Similarly, including one or more resistors and/or diodes onto the array may enable the array to provide protection to a monitor, a sensor and/or any other equipment connected thereto from electrostatic discharge (ESD). Protection against ESD may increase the reliability of the entire system and may prevent disruption of signals when ESD occurs.

Additionally or alternatively, the GSR arrays, disclosed herein, may include capacitors electrically connected between the active electrode and each or some of the plurality of inactive electrodes. If the capacitors connected to each inactive electrode are different, the time delay in the GSR measurement obtained from a particular inactive electrode may serve as a "finger print" of the electrode.

Additionally or alternatively, the GSR arrays, disclosed herein, may include a thermistor. Incorporation of a thermistor may enable evening out of values obtained due to thermoregulation rather than physiological arousal (e.g. pain) by calibrating the GSR readings to the subject's body temperature, changes in blood volume, basal perspiration, room temperature, environmental temperature, or combinations thereof. Furthermore, when a heat element is incorporated into the system, the thermistor may serve as an input indication and/or as a trigger to activation of the heat element.

Additionally or alternatively, the GSR arrays, disclosed herein, may include a piezoelectric sensor. Advantageously, the piezoelectric sensor may be arranged so as to enable determination of whether the finger attached to the array is kept straight, as a straight finger is important to the quality of the GSR measurements. According to some embodiments, more than one piezoelectric sensor may be included. Incorporation of two or more piezoelectric sensors may enable the extraction of pulse transient time (Ptt) readings. Additionally or alternatively, the Ptt readings may extracted from signals obtained from a conjunction of a piezoelectric sensor and a PPG sensor. Additionally or alternatively, the Ptt readings may be extracted from signals obtained from two or more spaced apart PPG sensors. The PPG sensor(s) and/or piezoelectric sensor(s) may be positioned such that the signals obtained are from a same arteriole i.e. at the bottom of the finger and at the tip of the finger.

Advantageously, the GSR electrode array disclosed herein is configured for attachment to and measurement from a single finger of the subject. This enables the array to be incorporated into a (single) finger probe and thus form an integral unit with additional sensors placed in the finger probe. In addition, this enables obtaining measurements from a plurality of sensors from a same finger thereby overcoming inaccuracies caused by obtaining measurements from different fingers.

Also disclosed herein are devices and methods configured to determine which of the plurality of inactive electrodes of the GSR electrode array has the optimal distance from the active electrode given the subject's skin dryness and/or finger length. Furthermore, once an optimal inactive electrode has been elected, the device and method disclosed herein enables measuring of the subject's GSR and changes therein while taking into consideration the distance between the active electrode and the elected inactive electrode.

According to some embodiments, there is provided a galvanic skin response (GSR) electrode array comprising a scaffold configured for attachment along a length of a subject's finger, the scaffold including an active electrode configured to provide an electrical signal, at least two inactive electrodes configured to collect the electrical signal transferred from the active electrode through the subject's body, and at least one element selected from a resistor, a capacitor, a piezoelectric sensor, a thermistor, a solenoid diode, or any combination thereof.

According to some embodiments, the at least two inactive electrodes may be positioned at a different predetermined distance from the active electrode.

According to some embodiments, the active electrode and each of the at least two measurement electrodes may be connectable to a finger probe through a connection point enabling transmittal of the electrical signal.

According to some embodiments, the active electrode may include a hydrogel configured to mediate contact between the active electrode and the subject's skin. According to some embodiments, the at least two inactive electrodes may include a hydrogel configured to mediate contact between the inactive electrodes and the subject's skin. According to some embodiments, the electrode array may further include a humidity sensor configured to sense the humidity of the hydrogel.

According to some embodiments, the element may be at least one resistor electrically connected to at least one of the at least two inactive electrodes. According to some embodiments, the element may be at least one resistor electrically connected to the active electrode.

According to some embodiments, the element may be configured to provide defibrillation protection to a monitor and/or to a sensor connected thereto. According to some embodiments, the element may be configured to protect a monitor and/or a sensor connected thereto from electrostatic discharge (ESD).

According to some embodiments, the element may be at least one capacitor electrically connected between the active electrode and one of the at least two inactive electrodes.

According to some embodiments, the element may be at least one piezoelectric sensor.

According to some embodiments, the element may be at least one thermistor.

According to some embodiments, the distance between the active electrode and a first of the at least two inactive electrodes may be different than the distance between the first electrode and a second of the at least two inactive electrodes.

According to some embodiments, the at least two inactive electrodes may be identical. According to some embodiments, the at least two inactive electrodes may be made from a different material. According to some embodiments, the at least two inactive electrodes may have a different size and/or shape.

According to some embodiments, the electrode array may further include at least one heating element configured to heat the subject's finger.

According to some embodiments, the electrode array may further include at least one sensor selected from a PPG sensor, an accelerometer, a temperature sensor, a diffused correlation spectroscopy (DCS) sensor, an acoustics sensor, a bio-impedance sensor, a piezoelectric sensor, and any combination thereof.

According to some embodiments, the electrode array may further include a pocket and at least one strap which, when pulled, may be configured to generate a vacuum in the pocket, thereby sucking in a skin of the subject in contact with the pocket.

According to some embodiments there is provided a finger probe including at least one sensor selected from a PPG sensor, an accelerometer, a temperature sensor, a diffused correlation spectroscopy (DCS) sensor, an acoustics sensor, a bio-impedance sensor, a piezoelectric sensor, and any combination thereof, and a connection point connectable to a GSR electrode array.

According to some embodiments, the connection point may be configured to provide an electrical signal to an active electrode positioned on the electrode array and to transmit the electrical signal received from at least one inactive electrode positioned on the electrode array.

According to some embodiments, the finger probe may further include an open electrical circuit configured to be closed when the electrode array is connected to the connection point. According to some embodiments, only when the electrode array is connected to the connection point is the at least one sensor activated According to some embodiments, the finger probe may include at least two sensors. According to some embodiments, the at least two sensors may include a PPG sensor, an accelerometer and temperature sensor, a diffused correlation spectroscopy (DCS) sensor, an acoustics sensor, a bio-impedance sensor, a piezoelectric sensor, and any combination thereof. According to some embodiments, the finger probe may include at least two PPG sensors. According to some embodiments, the at least two PPG sensors may be positioned within the finger probe so as to enable extraction of pulse transient time (Ptt) readings when in use. According to some embodiments, the finger probe may include at least a PPG sensor and a piezoelectric sensor. According to some embodiments, the PPG sensor and the piezoelectric sensor may be positioned within the finger probe so as to enable extraction of pulse transient time (Ptt) readings when in use. According to some embodiments, the finger probe may include at least two piezoelectric sensors. According to some embodiments, the at least two piezoelectric sensors may be positioned within the finger probe so as to enable extraction of pulse transient time (Ptt) readings when in use.

According to some embodiments, the finger probe may further include a humidity sensor configured to sense a humidity of a hydrogel.

According to some embodiments, the finger probe may at least include more than one PPG sensor enabling extraction of pulse transient time (Ptt) readings. Additionally or alternatively, the finger probe may at least include more than one piezoelectric sensor enabling extraction of pulse transient time (Ptt) readings. Additionally or alternatively, the finger probe may at least include a PPG sensor and a piezoelectric sensor enabling extraction of pulse transient time (Ptt) readings. According to some embodiments, the, PPG sensor(s) and/or piezoelectric sensor(s) may be spaced apart such that the signals obtained are from a same arteriole, i.e. at the bottom of the finger and at the tip of the finger. It is understood that the PPG sensor(s) and/or piezoelectric sensor(s) may be directly attached to or mounted on the finger probe, the GSR array or a combination thereof.

According to some embodiments, there is provided a medical device configured to determine the electrical conductance of a subject's skin. According to some embodiments, the device includes a processor configured to receive an electrical signal from a GSR electrode array, the GSR electrode array configured for attachment along a length of a subject's finger and having an active electrode and at least two inactive electrodes, wherein each of the at least two inactive electrodes are positioned at a different predetermined distance from the active electrode; determine a preferred inactive electrode among the at least two inactive electrodes based on the received electrical signal; and determine the electrical conductance of the subject's skin based on an integrated analysis of the electrical signal received from the preferred inactive electrode and on a distance between the active electrode and the preferred electrode.

According to some embodiments, determining the electrical conductance of the subject's skin may include providing a weight factor to the received electrical signal, the weight factor determined based on the distance between the active electrode and the preferred electrode.

According to some embodiments, the processor may further be configured to determine a change in the electrical conductance of the subject's skin based on a change in the electrical signal obtained in a first measurement and a second measurement and based on the distance between the active electrode and the preferred electrode.

According to some embodiments, the medical device may further be configured to determine a pain level of the subject and/or a change therein based on the determined electrical skin conductance and on at least one physiological signal. According to some embodiments, the physiological signal may be selected from Photoplethysmograph (PPG), Galvanic Skin Response (GSR); electrocardiogram (ECG), blood pressure, respiration, internal body temperature, skin temperature, electrooculography (EOG), pupil diameter, electroencephalogram (EEG), frontalis electromyogram (FEMG), electromyography (EMG), electro-gastro-gram (EGG), laser doppler velocimetry (LDV), partial pressure of carbon dioxide, and accelerometer readings.

According to some embodiments, there is provided a method for determining the electrical conductance of a subject's skin, the method including: receiving an electrical signal from a GSR electrode array having a plurality of inactive electrodes, determining a preferred inactive electrode among the plurality of inactive electrodes based on the received electrical signal; and determining the electrical conductance of the subject's skin based on an integrated analysis of an electrical signal received from the preferred inactive electrode and on a distance between the active electrode and the preferred inactive electrode.

According to some embodiments, there is provided a method for determining a value of a physiological parameter, the method including: applying an alternative current (AC) excitation at a changing frequency to an active electrode; measuring a first electrical signal obtained from a first inactive electrode after a first predetermined time; measuring a second electrical signal obtained from a second inactive electrode after a second predetermined time; and determining the value of the physiological parameter based on the first and second electrical signals.

According to some embodiments, the physiological parameter may be a hemodynamic parameter selected from blood flow, heart rate, pulse transient time (PTT) and any combination thereof.

According to some embodiments, the physiological parameter may be respiration parameter, selected from respiration rate, apnea, fast/slow changes in the respiration, and any combination thereof.

According to some embodiments, determining the value of the physiological parameter may further include obtaining at least one signal from any one or more of a PPG sensor, from a piezoelectric sensor, a diffused correlation spectroscopy (DCS) sensor, an acoustics sensor, a bio-impedance sensor, and/or temperature sensor.

According to some embodiments, there is provided a method for determining a value of a physiological parameter, the method including obtaining signals from at least two sensors, and determining the value of the physiological parameter based on the obtained signals. According to some embodiments, the at least two sensors may include a PPG sensor, a piezoelectric sensor or any combination thereof. According to some embodiments, the physiological parameter may be a hemodynamic parameter selected from blood flow, heart rate, pulse transient time (Ptt) and any combination thereof. According to some embodiments, the at least two sensors may be positioned within a finger probe. According to some embodiments, the at least two sensors may be spaced apart along a longitudinal axis of the finger probe. According to some embodiments, a first of the at least two sensors may be positioned at a proximal end of the finger probe and a second of the at least two sensors may be positioned at a distal end of the finger probe.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced. The figures are for the purpose of illustrative discussion and no attempt is made to show structural details of an embodiment in more detail than is necessary for a fundamental understanding of the teachings of the disclosure. For the sake of clarity, some objects depicted in the figures are not to scale.

FIG. 2A-2F schematically illustrate a front side of a GSR electrode array with an active electrode and a plurality of inactive electrodes disposed along a longitudinal axis thereof, according to some embodiments;

DETAILED DESCRIPTION

Figure 1A:
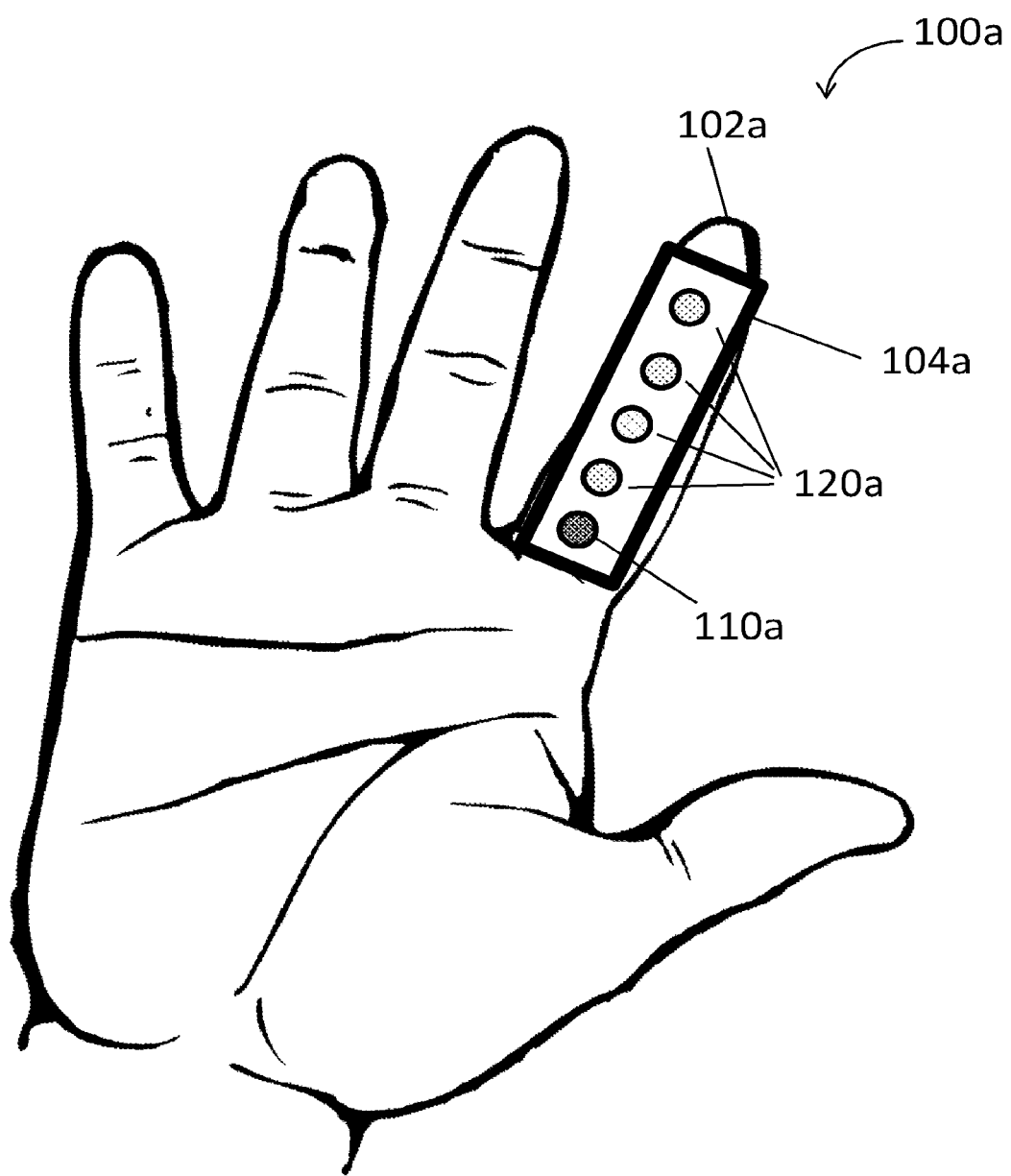
FIG. 1A schematically illustrates a GSR electrode array attached along a length of a subject's finger, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided an array of electrodes for monitoring of physiological parameters. According to some embodiments, the array of electrodes may be a galvanic skin response (GSR) electrode array. According to some embodiments, the array may include a scaffold configured for attachment to a subject, for example along a length of a subject's finger. The scaffold may include an active electrode configured to provide an electrical signal and a plurality of inactive electrodes configured to collect the electrical signal transferred from the active electrode through the body of the subject. According to some embodiments, one or more of the plurality of electrodes (active or inactive) may serve as a reference electrode. According to some embodiments, the scaffold my further include an additional electrode serving as reference electrodes.

As used herein, the term "GSR electrode array", "GSR array" and "array" may be used interchangeably. The GSR electrode array is an array of electrodes used for monitoring skin conductance and/or resistance. According to some embodiments, during a measurement, only one active electrode and one inactive electrode of the array (or optionally more than one active or inactive electrodes) may be utilized. According to some embodiments, the array may be disposable. According to some embodiments, the array may be reusable.

As used herein, the term "scaffold" may refer to any suitable mounting configured to be attached to a subject's finger, hand palm, foot or forehead and to have disposed thereon or therein a plurality of electrodes at defined locations. According to some embodiments, the scaffold may be a sticker having a cover which when pulled off exposes the sticker. According to some embodiments, the scaffold may be a fabric (woven or plastic) comprising fasteners or other means for attachment to a patient's finger. According to some embodiments, the scaffold may include an air pocket and one or more straps which, when pulled, generate a vacuum which consequently will suck in the skin of the subject's finger, and thereby ensure adequate contact between the skin and the electrodes of the scaffold. The attachment of the array may include attaching the scaffold to the skin, for example as a sticker, and then, by pulling a strap, generating a vacuum which sucks in the skin, thereby enhancing the attachments of the scaffold to the skin. It is understood by one of ordinary skill in the art that a major problem when measuring galvanic skin response is the electrode contact with the human body. By creating a vacuum, the adhesiveness of the electrode to the finger may ensure firm attachment of the electrode array to the subject's skin for a prolonged period. It is further understood that such firm attachment may serve to ensure an optimal interface between the skin and the electrodes.

As used herein, the terms "active electrode" and "source electrode" may be interchangeably used and refer to the electrode on which an electrical signal, e.g. a voltage, is applied. It is understood by one of ordinary skill in the art that any of the electrodes on the array may serve as the active electrode when connected to a power supply.

As used herein, the term "inactive electrode" and "measurement electrode" may be interchangeably used and refer to the electrode which receives an electrical signal (e.g. an electrical current) transmitted from the active electrode. As used herein, the term "plurality" when referring to inactive electrodes may refer to 2, 3, 4, 5, 10 or more electrodes. Each possibility is a separate embodiment.

As used herein, the term "reference electrode" refers to an electrode configured to provide measurements that serve as a reference point to measurements obtained from an inactive electrode and/or or an electrode configured to provide a certain voltage level to the whole measurement.

According to some embodiments, the plurality of inactive electrodes may be identical. Alternatively, the plurality of inactive electrodes may be different. For example, the inactive electrodes may be made from a different material. Suitable materials include gold, gold-plated copper, nickel-plated metal, platinum, palladium and silver-silver chloride. Each possibility is a separate embodiment. Additionally or alternatively, the inactive electrodes may be of a different size and/or shape. According to some embodiments, the material of which the electrode is made as well as its size and/or shape may influence the monitored signal and may thus serve as an identification means of the electrode and its distance from the active electrode.

According to some embodiments, the active electrodes and each of the plurality of inactive electrodes may be spaced apart from one another on the scaffold, for example on a longitudinal axis thereof. According to some embodiments, each of the plurality of inactive electrodes may be positioned at a different predetermined distance from the active electrode. The plurality of inactive electrodes on the array may enable choosing a specific inactive electrode from the plurality of inactive electrodes, having a preferred distance from the active electrode. This may enable taking into account inter person differences in skin dryness as well as adjusting to differences in skin humidity owing, for example, to differences in body temperature and/or taking into consideration the length of the subject's finger. As a non-limiting example, an electrode closer to the active electrode may be elected for subjects with dry skin. As another non-limiting example, a further spaced apart electrode may be elected when body temperature is high (for example due to warm weather, high environmental temperature or differences in the physical activity of the subject during or prior to monitoring).

According to some embodiments, the distance between each electrode and its neighboring electrodes may be constant, gradually increasing, gradually decreasing or random. Each possibility is a separate embodiment. It is understood to one of ordinary skill in the art that as the distance between the active electrode and the inactive electrode is being increased, everything else being equal, the current measured at the inactive electrode will be lower and thus more susceptible to noise. Accordingly, according to some embodiments, the density of inactive electrodes may be lower as the distance to the active electrode is increased. This may enable saving of the total amount of electrodes applied to the array and thus save on cost of production of the entire array. Alternatively, the density of inactive electrodes may be higher as the distance to the active electrode is decreased, since the distance typically is decreased when signal quality at a larger distance is low. Again, the uneven spreading of electrodes on the scaffold may enable saving of the total amount of electrodes incorporated into the array and thus on the cost of production thereof.

According to some embodiments, the distance of each electrode from the active electrode is predetermined and known. Thus, its impact on the monitored electrical signal and on the changes therein can be taken into consideration when calculating changes in the conductivity of the skin. For example, when the inactive electrode is located relatively close to the active electrode, the sensitivity to changes in the monitored electrical signal is decreased. Accordingly, according to some embodiments, different multipliers may be applied to measurement obtained depending on the distance of the utilized inactive electrode from the active electrode.

According to some embodiments, the GSR electrode array, disclosed herein, includes a scaffold having an active electrode and a plurality of inactive electrodes disposed thereon. The electrodes are positioned on the scaffold so that each inactive electrode is located at a different predetermined distance from the active electrode. On the one hand, this enables customizing of the distance between the active electrode and the inactive electrode to accommodate differences in skin dryness, while on the other hand, given the distance being known, its impact on the measured value can be taken into consideration when determining changes in the conductivity of the skin.

According to some embodiments, the GSR electrode array may be configured to enable GSR monitoring from a finger, a hand palm, a foot, a forehead or any other suitable position on a subject. Each possibility is a separate embodiment. According to some embodiments, the GSR electrode array may be configured to enable GSR monitoring from a single finger of the subject. According to some embodiments, the GSR electrode array may be connectable to a finger probe.

According to some embodiments, the array may be an array for monitoring a plurality of physiological signals and may thus include additional sensors in addition to the GSR electrodes. Non-limiting examples of suitable sensors include a PPG sensor, an accelerometer, a temperature sensor, a DCS (diffused correlation spectroscopy) sensor, an acoustics sensor, a bio-impedance sensor, a piezoelectric sensor, or any other suitable sensor of physiological parameters. Each possibility is a separate embodiment. Accordingly, the GSR electrode array may, according to some embodiments, form an integral unit with additional sensors placed within the finger probe and/or being part of the array.

According to some embodiments, the array may further include a memory component. According to some embodiments, the memory component may enable a calibration of sensors on the array, such as, but not limited to, the GSR electrodes or the piezoelectric sensor. According to some embodiments, the memory component may be configured to store subject specific data, such as, but not limited to, age, weight, skin humidity, medical history, or any other suitable data. Each possibility is a separate embodiment. According to some embodiments, the memory component may provide a unique signature for the array.

According to some embodiments, the active electrode and each of the plurality of inactive electrodes (and optionally reference electrode(s)) may be connectable to one or more connection points placed within a finger probe. The connection point may be configured to allowing transmittal of the electrical signal.

As used herein, the term "connection point" may refer to a point of attachment of the array to the finger probe and may be configured to transfer an electric signal between the electrode(s) and sensor and/or monitor of a medical device. According to some embodiments, each electrode may have its own connection point. According to some embodiments, the connection point may receive an electrical signal from a plurality of electrodes, each electrode having a separate electrical wire running through the connection point. According to some embodiments, the connection point may be configured to allow wires of additional sensors (e.g. a PPG sensor or a humidity sensor) to run therethrough.

According to some embodiments the active electrodes, inactive electrodes and/or additional electrodes may be dry electrodes, such as, but not limited to, silver chloride electrodes. GSR monitoring requires a stable and consistent skin contact. Accordingly, according to some embodiments, the active electrode and each of the inactive electrodes and/or additional electrodes, such as reference electrodes, may be disposed within or attached to a compartment including a hydrogel configured to mediate contact between the electrode and the subject's skin. According to some embodiments, the GSR electrode array (e.g. the scaffold) may include a humidity sensor configured to sense the humidity of the hydrogel. This may be of particular relevance in long-term GSR monitoring during which the hydrogel may dry and thus cause a reduction in signal quality. According to some embodiments, the signal obtained from the humidity sensor may serve as an indication that replacement of the GSR array is needed. Furthermore, long-term storage of GSR arrays or storage in suboptimal conditions may cause drying out of the hydrogel prior to use. Hence, according to some embodiments, the signal obtained from the humidity sensor may serve as an indication of hydrogel quality. According to some embodiments, the GSR array may be configured to allow addition of hydrogel to the hydrogel compartment. According to some embodiments, the signal obtained from the humidity sensor may serve as an indication that addition of hydrogel is required, thereby eliminating the need for exchanging the entire array.

According to some embodiments, the GSR array may include at least one electrical element selected from a resistor, a capacitor, a piezoelectric sensor, a thermistor, a solenoid diode, or any combination thereof. Each possibility is a separate embodiment. As used herein, the term "at least one" when referring to electrical elements, may include 1, 2, 3, 4, 5 or more elements. Each possibility is a separate embodiment.

For example, according to some embodiments, the GSR electrode array may include one or more resistors electrically connected to at least one of the plurality of inactive electrodes. Additionally or alternatively, the resistor may be electrically connected to the active electrode. Alternatively, the resistor may be part of an electric circuit, separate from the electric circuit of the electrodes on the array.

For example, according to some embodiments, the GSR electrode array may include one or more diodes electrically connected to at least one of the plurality of inactive electrodes. Additionally or alternatively, the diode may be electrically connected to the active electrode. Alternatively, the diode may be part of an electric circuit, separate from the electric circuit of the electrodes on the array.

According to some embodiments, the one or more resistors and/or diodes may be used to provide at least a partial defibrillation protection to a monitor, a sensor or any other equipment connected to the array and to a power supply. Implementing the defibrillation protection on the electrode array may enable using the array with systems devoid of defibrillation protection. As used herein the term "defibrillation protection" may refer to any mechanism allowing for a medical equipment to remain attached to a patient during defibrillation and thus to any mechanism enabling the equipment to withstand a pulse without causing an unacceptable risk.

According to some embodiments, the one or more resistors and/or diodes may be configured to protect a monitor and/or a sensor connected thereto from electrostatic discharge (ESD). As used herein, the terms "Electrostatic discharge" and "ESD" may be used interchangeably and may refer to the sudden flow of electricity between two electrically charged objects caused by contact, an electrical short or dielectric breakdown. It is understood to one of ordinary skill in the art that ESD may cause damage to sensitive electronic devices. Thus, protection against ESD may increase the reliability of the entire system and may prevent disruption of signals when ESD occurs.

According to some embodiments, the resistor may enable shifting of the electrical signal to be compatible with an applied measurement range. A resistor may, for example, be connected to each or some of the plurality of inactive electrodes so as to harmonize their measurement scale. According to some embodiments, each inactive electrode may be electrically connected to a resistor of different resistor value. For example, the inactive electrode spaced furthest away from the active electrode, which is typically elected in subjects with high skin humidity, may be electrically connected to a resistor with a higher value than the electrode closest to the active electrode, typically elected in subjects with very dry skin. According to some embodiments, the resistor may serve as an identification mark of the electrode and of its distance from the active electrode.

Additionally or alternatively, the GSR electrode array may include one or more capacitors, each capacitor electrically connected between the active electrode and one of the plurality of inactive electrodes. If the capacitors connected to each inactive electrode have a different capacity value, the time delay in the GSR measurement obtained from each electrode will differ and may thus serve as a "finger print" of the electrode.

Additionally or alternatively, the GSR electrode array may include one or more piezoelectric sensors. According to some embodiments, the piezoelectric sensor may be so arranged as to enable determining whether the finger to which the GSR electrode array is attached is kept straight. This may ensure high quality monitoring as a straight finger is imperative to the quality of the GSR measurements since it ensures a fixed distance between the electrodes and optimizes the attachment of the electrodes to the skin.

Furthermore, incorporation of two or more piezoelectric sensors may enable the extraction of pulse transient time (Ptt) readings. Additionally or alternatively, the Ptt readings may extracted from signals obtained from a conjunction of a piezoelectric sensor and a PPG sensor. Additionally or alternatively, the Ptt readings may be extracted from signals obtained from two or more spaced apart PPG sensors. The PPG sensor(s) and/or the piezoelectric sensor(s) may be so positioned such that the signals are from a same arteriole i.e. at the bottom of the finger and at the tip of the finger.

Additionally or alternatively, the GSR electrode array may include one or more thermistors. Incorporation of a thermistor may enable determination of a subject's body temperature and, in turn, even out values obtained due to thermoregulation rather than physiological arousal (e.g. pain). Additionally or alternatively, the incorporation of a thermistor may enable taking into consideration changes in blood volume, basal perspiration, room temperature, environmental temperature, or combinations thereof, when determining a level of physiological arousal (e.g. pain). Each possibility is a separate embodiment.

According to some embodiments, the GSR electrode array may include one or more heating elements configured to heat the finger (or other attachment point such as, but not limited to, a hand palm, a foot or a forehead). Heating the subject's finger may be advantageous when the conductivity of the skin is low and/or when the GSR signal is of poor quality. Moreover, heating the subject's finger may further serve to improve PPG readings. According to some embodiments, the activation of the heating element may be controlled by the signal obtained from the thermistor. According to some embodiments, the heating element may be automatically activated when the determined body temperature is low.

According to some embodiments, there is provided a finger probe including at least one sensor and one or more connection points, allowing connection of a GSR sensor, such as, but not limited to, the GSR array disclosed herein. According to some embodiments, the probe may be a "hand probe" enabling measurements to be taken from the hand palm.

As used herein, the term "finger probe" may refer to casing configured to receive a finger of a subject. The casing may be made of any suitable material, which preferably is comfortable to the subject so as to cause minimum unease. According to some embodiments, the casing material may be flexible (e.g. rubber), however, according to alternative embodiments, a more rigid material may be used for the probe casing. According to some embodiments, the casing may be made from a dark material or any other material preventing surrounding light to enter the casing and thus affect measurements, such as, but not limited to, PPG measurements, According to some embodiments, the casing may be configured to encompass therein a single finger only. According to some alternative embodiments, the casing may be configured to encompass therein more than one finger, such as two fingers of the same hand. According to yet an alternative embodiment, the casing may be configured to receive the entire hand palm.

As used herein, the term "at least one", when referring to sensors, may include 1, 2, 3, 4, 5 or more sensors. Each possibility is a separate embodiment. Non-limiting examples of suitable sensors include a PPG sensor, an accelerometer, a temperature sensor a diffused correlation spectroscopy (DCS) sensor, an acoustics sensor, a bio-impedance sensor, a piezoelectric sensor, or any other suitable sensor of physiological parameters or combinations thereof. Each possibility is a separate embodiment.

According to some embodiments, the connection point of the finger probe may be configured to transmit an electrical signal from a power source to an active electrode of a GSR sensor, such as, but not limited to, the active electrode of the GSR electrode array disclosed herein. According to some embodiments, the connection point (same or different) may be configured to allow transmission of an electrical signal (e.g. an electrical current) received from one or more inactive electrodes, such as, but limited to, one or more of the plurality of inactive electrodes of the GSR electrode array, to a detection device (e.g. an ammeter).

According to some embodiments, the at least one sensor is electrically connected to the finger probe in an open electrical circuit in such manner that even when connected to an active power supply, the sensor remains shut off. According to some embodiments, connection of the GSR sensor, such as, but not limited to, the GSR electrode array disclosed herein, may serve as a trigger for activation of the at least one sensor placed within the finger probe (e.g. the PPG sensor). According to some embodiments, the finger probe and the at least one sensor incorporated therein may be configured to enable measurements only when a GSR sensor (e.g. the GSR electrode array disclosed herein) is attached to the connection point. According to some embodiments, connection of the GSR array to the connection point of the finger probe may push upon a bottom which consequently closes the electrical circuit of the at least one sensor of the finger probe and thus cause its activation. According to some embodiments, the GSR array may include a conductive material which, upon connection of the GSR array to the connection point, closes the electrical circuit of the at least one sensor of the finger probe and thus cause its activation. Such arrangement may ensure that monitoring, which requires obtaining signals from a GSR sensor (which may not be an integral part of the finger probe) in addition to signals obtained from the at least one sensor incorporated in the finger probe, will not mistakenly be performed without attachment of the GSR sensor.

According to some embodiments, the finger probe may include an open electrical circuit configured to be closed only when a subject's finger is correctly positioned within the finger probe. This may serve to ensure that no measurements are made prior to the subject's finger being correctly placed within the finger probe casing. For example, when the subject's finger is correctly positioned within the finger probe casing, the finger may pressure upon a contact, a pressure button or any other suitable element capable of closing the electrical circuit. It is understood to one of ordinary skill in the art that such configuration may prevent false readings, which may lead to sometimes even fatal medical decisions. According to some embodiments, this may also ensure that measurements will be discontinued when the subject's finger is removed from the finger probe.

According to some embodiments, the finger probe may further include a humidity sensor configured to sense a humidity of a GSR electrode hydrogel, such as, but not limited to, the hydrogel of the electrodes of the GSR electrode array disclosed herein. Alternatively, the humidity sensor may an electrical circuit monitoring the humidity of the hydrogel based on the conductance of the hydrogel. Yet alternatively, the humidity sensor may monitor the humidity of the hydrogel based on the quality of the GSR signal. Monitoring hydrogel humidity may be of particular relevance in long-term monitoring, during which the hydrogel may dry and thus cause a reduction in signal quality. According to some embodiments, the humidity sensor may be configured to provide a signal, which may indicate whether replacement of the GSR array is needed. Furthermore, long-term storage of GSR arrays or storage in suboptimal conditions may cause drying out of the hydrogel, or otherwise reduce hydrogel quality, prior to use. Hence, according to some embodiments, the signal obtained from the humidity sensor may serve as an indication of hydrogel quality. According to some embodiments, the GSR array may be configured to allow addition of hydrogel to the hydrogel compartment. According to some embodiments, the signal obtained from the humidity sensor may serve as an indication that addition of hydrogel is required, thereby eliminating the need for exchanging the entire array.

According to some embodiments, the finger probe may further include a temperature sensor configured to sense external (room) temperature.

According to some embodiments, the finger probe may further include a memory component. According to some embodiments, the memory component may be configured to store subject specific physiological parameters and/or data, such as, but not limited to, age, weight, skin humidity, medical history or any other suitable data or combinations thereof. Each possibility is a separate embodiment. According to some embodiments, the memory component may include and/or have stored therein normalization parameters used to normalize an obtained signal. According to some embodiments, the memory component may be configured to transfer the subject specific parameters/data and/or the normalization parameters to a medical device. According to some embodiments, the memory component may be configured to transfer the subject specific parameters/data and/or the normalization parameters to a remote computer, thereby facilitating transfer of data, for example, from an operating room (OR) to a post-anesthesia care unit (PACU), or from PACU to General floor.

According to some embodiments, there is provided a medical device configured to determine electrical conductance of a subject's skin, the device including a processor configured to receive an electrical signal from a GSR electrode array or from a finger probe including same, to determine a preferred inactive electrode among a plurality of inactive electrodes on the GSR electrode array based on the received electrical signal; and to determine the electrical conductance of the subject's skin based on an integrated analysis of an electrical signal received from the preferred inactive electrode and on a distance between the active electrode and the preferred inactive electrode.

According to some embodiments, the array may be configured for attachment along a length of a subject's finger and may include an active electrode and a plurality of inactive electrodes, wherein the active electrode and the plurality of inactive electrodes may be spaced apart along a longitudinal axis of the array, as essentially described herein.

According to some embodiments, when the array is placed correctly and firmly on the patient finger a voltage (direct or alternating) may be applied to the active electrode whereafter measurements may be taken from the inactive electrodes. It is understood that alternatively a current may be applied, in which case the potential induced on the inactive electrode is measured.

According to some embodiments, the preferred electrode may be determined based on simultaneous or sequential measurements obtained from all of the plurality of inactive electrodes, for example, by electing the electrode with the best signal.

According to some embodiments, the preferred electrode may be determined based on a signal obtained from a predetermined first inactive electrode, e.g. the center most inactive electrode. The preferred electrode may then be determined to be an inactive electrode closer to the active electrode, an inactive electrode further distanced from the active electrode or the initially chosen inactive electrode. Each possibility is a separate embodiment. For example, in case the signal is too low, the device may be configured to elect an inactive electrode closer to the active electrode. If oppositely, the signal is saturated, the device may be configured to elect an inactive electrode further away from the active electrode.

According to some embodiments, the preferred electrode may be determined based on a preferred distance between the active electrode and the inactive electrode, the preferred distance determined and/or calculated based on the signal obtained from a predetermined, initially chosen, inactive electrode.

Once an optimal inactive electrode has been elected, the device may enable measuring of the subject's GSR and changes therein while taking into consideration the distance between the active electrode and the elected inactive electrode. Since the distance between the active electrode and each of the plurality of inactive electrodes is predetermined and known, its impact on the monitored electrical signal and on the changes therein can be taken into consideration when calculating the skin conductivity and/or changes therein. For example, when the elected inactive electrode is located relatively close to the active electrode, the sensitivity to changes in the monitored electrical signal is decreased. For example, when the elected inactive electrode is located relatively distant to the active electrode, the sensitivity to changes in the monitored electrical signal is increased. Accordingly, according to some embodiments, different multipliers may be applied to measurements obtained depending on the distance of the utilized inactive electrode from the active electrode.

According to some embodiments, the processor may be configured to determine changes in the electrical conductance of the subject's skin. According to some embodiments, the change in the subject's skin conductance may be determined based on changes in the electrical signal obtained during subsequent measurements and based on the distance between the active electrode and the preferred electrode. It is understood that the level of skin conductance, as well as the changes therein, may be influenced by the distance between the active electrode and the inactive electrode, as essentially described herein. According to some embodiments, the changes in the subject's skin conductance may be owing to changes in the subject's level of pain.

It is known to one of ordinary skill in the art that, changes in external temperature may influence skin conductivity. Hence, according to some embodiments, the device disclosed herein may be configured to adjust the signal baseline (i.e. baseline skin conductivity) based on changes in external temperature. According to some embodiment, the device may be configured to reelect a new preferred inactive electrode, for example, based on a determined change in the room temperature. It is understood, that once a new inactive electrode is elected, an algorithm for calculating the GSR and the changes therein is updated to take into consideration the change in the distance between the active electrode and the newly chosen inactive electrode.

According to some embodiments, the device may be configured to determine a pain level of a subject and/or a change therein based on the determined electrical skin conductance and/or changes therein and on at least one physiological signal.

According to some embodiments, the at least one physiological signal may be selected from: Photoplethysmograph (PPG), Galvanic Skin Response (GSR); electrocardiogram (ECG), blood pressure, respiration, internal body temperature, skin temperature, electrooculography (EOG), pupil diameter, electroencephalogram (EEG), frontalis electromyogram (FEMG), electromyography (EMG), electro-gastro-gram (EGG), laser doppler velocimetry (LDV), diffused correlation spectroscopy, acoustics, bio-impedance, piezo-electricity, partial pressure of carbon dioxide, accelerometer readings, or any combination thereof. Each possibility is a separate embodiment.

According to some embodiments, there is provided a method for determining electrical conductance of a subject's skin, the method including receiving an electrical signal from a GSR electrode array, determining a preferred inactive electrode among the plurality of inactive electrodes based on the received electrical signal; and determining the electrical conductance of the subject's skin based on an integrated analysis of an electrical signal received from the preferred inactive electrode and on a distance between the active electrode and the preferred inactive electrode.

According to some embodiments, determination of a preferred electrode may be based on simultaneous or sequential measurements obtained from all of the plurality of inactive electrodes, for example, by electing the electrode with the best signal. Each possibility is a separate embodiment.

According to some embodiments, determination of a preferred electrode may be based on a signal obtained from a predetermined first inactive electrode, e.g. the center most inactive electrode. The preferred electrode may then be determined to be an inactive electrode closer to the active electrode, an inactive electrode further distanced from the active electrode or the initially chosen inactive electrode. Each possibility is a separate embodiment. For example, in case the signal is too low, an inactive electrode closer to the active electrode may be elected. If oppositely, the signal is saturated, an inactive electrode further away from the active electrode may be elected.

According to some embodiments, determination of a preferred electrode may be based on a preferred distance between the active electrode and the inactive electrode. According to some embodiments, the preferred distance may be determined and/or calculated based on the signal obtained from a predetermined initially chosen inactive electrode.

Once an optimal inactive electrode has been elected, the subject's GSR and changes therein may be determined while taking into consideration the distance between the active electrode and the elected inactive electrode. Since the distance between the active electrode and each of the plurality of inactive electrodes is predetermined and known, its impact on the monitored electrical signal and on the changes therein can be taken into consideration. For example, when the elected inactive electrode is located relatively close to the active electrode, the sensitivity to changes in the monitored electrical signal is decreased. For example, when the elected inactive electrode is located relatively distant to the active electrode, the sensitivity to changes in the monitored electrical signal is increased. Accordingly, according to some embodiments, the method may include applying different multipliers to measurements obtained depending on the distance of the utilized inactive electrode from the active electrode.

According to some embodiments, the method may include determining changes in the electrical conductance of the subject's skin. According to some embodiments, the change in the subject's skin conductance may be determined based on changes in the electrical signal obtained during subsequent measurements and based on the distance between the active electrode and the preferred electrode. It is understood that the level of skin conductance, as well as the changes therein, may be influenced by the distance between the active electrode and the inactive electrode, as essentially described herein. According to some embodiments, the changes in the subject's skin conductance may be owing to changes in the subject's level of pain.

According to some embodiments, the method may include adjusting the signal baseline (i.e. baseline skin conductivity) based on changes in external temperature. According to some embodiments, may include electing a new preferred inactive electrode based on a determined change in the room temperature. It is understood that once a new inactive electrode is elected, the method for calculating the GSR and the changes therein is updated to take into consideration the change in the distance between the active electrode and the newly chosen inactive electrode.

According to some embodiments, there is provided a method for determining electrical conductance of a subject's skin, the method including placing a GSR array (or a probe containing same) on a subject's finger, applying a voltage to an active electrode and subsequently taking measurements from an inactive electrode. In case the signal is too low, the inactive electrode, from which a measurement is taken, may be changed to an inactive electrode closer to the active electrode. In case the signal is saturated, the inactive electrode, from which a measurement is taken, may be changed to an inactive electrode further distanced from the active electrode. According to some embodiments, during the measurement, the signal baseline level may change (e.g. due to changes in environmental temperature). According to some embodiments, the method includes continuously checking the signal level and optimizing the signal by changing the inactive electrode from which measurements are taken.

According to some embodiments, there is provided a method for determining a pain level of a subject and/or a change therein based on a determined electrical skin conductance and/or changes therein and on at least one physiological signal. According to some embodiments, the electrical skin conductance may be determined based on an integrated analysis of an electrical signal received from a preferred inactive electrode, chosen from among a plurality of inactive electrodes of a GSR electrode array (each spaced apart at a different distance from the active electrode) and on the distance between the active electrode and the preferred inactive electrode, as essentially described herein.

According to some embodiments, the at least one physiological signal may be selected from: Photoplethysmograph (PPG), Galvanic Skin Response (GSR); electrocardiogram (ECG), blood pressure, respiration, internal body temperature, skin temperature, electrooculography (EOG), pupil diameter, electroencephalogram (EEG), frontalis electromyogram (FEMG), electromyography (EMG), electro-gastro-gram (EGG), laser doppler velocimetry (LDV), diffused correlation spectroscopy, acoustics, bio-impedance, piezo-electricity, partial pressure of carbon dioxide, accelerometer readings or any combination thereof. Each possibility is a separate embodiment.

According to some embodiments, there is provided a method for determining a value of a physiological parameter by applying AC excitation at different frequencies to an active electrode. Measurements can then be obtained from each of a plurality of inactive electrodes (for example, from an electrode array as described herein) at different points of time, thereby obtaining a different depth of measurement, thereby enabling the extraction of physiological parameters from the measurements of different depth.

According to some embodiments, the physiological parameter may be a hemodynamic parameter, such as, but not limited to, blood flow, heart rate, blood volume, pulse transient time (PPT) or any combination thereof. Each possibility is a separate embodiment. According to some embodiments, the physiological parameter may be a respiration parameter, such as, but not limited to, respiration rate, apnea, fast/slow changes in the respiration or any combination thereof. Each possibility is a separate embodiment.

According to some embodiments, determining the values of the physiological parameter may further be based on signals obtained from a PPG sensor, from a piezoelectric sensor, a diffused correlation spectroscopy (DCS) sensor, an acoustics sensor, a bio-impedance sensor or any combination of one or more of each of the sensors. Each possibility is a separate embodiment.

Reference is now made to FIG. 1A, which schematically illustrates a GSR electrode array 100a attached along a length of a subject's finger 102a, according to some embodiment. GSR electrode array 100a includes a scaffold 104a, an active electrode 110a and a plurality of inactive electrodes 120a (here illustrated as 4 inactive electrodes). GSR electrode array 100a may further include at least one additional element, such as a resistor, a capacitor, a piezoelectric sensor, a thermistor, a solenoid diode or any combination thereof, as further described hereinbelow. It is understood to one of ordinary skill in the art that any of the electrodes on the array may serve as the active electrode and the designation as an active electrode is based on the connection to a power/energy source only. It is further understood that the position of the active electrode as being closest to the hand palm is illustrative only and a different arrangement (for example, the active electrode being the distant most electrode) is likewise possible and thus falls within the scope of this disclosure. It is further understood that the electrodes face the finger of the subject and may not be visible when the array is attached to the finger.

Figure 1B:
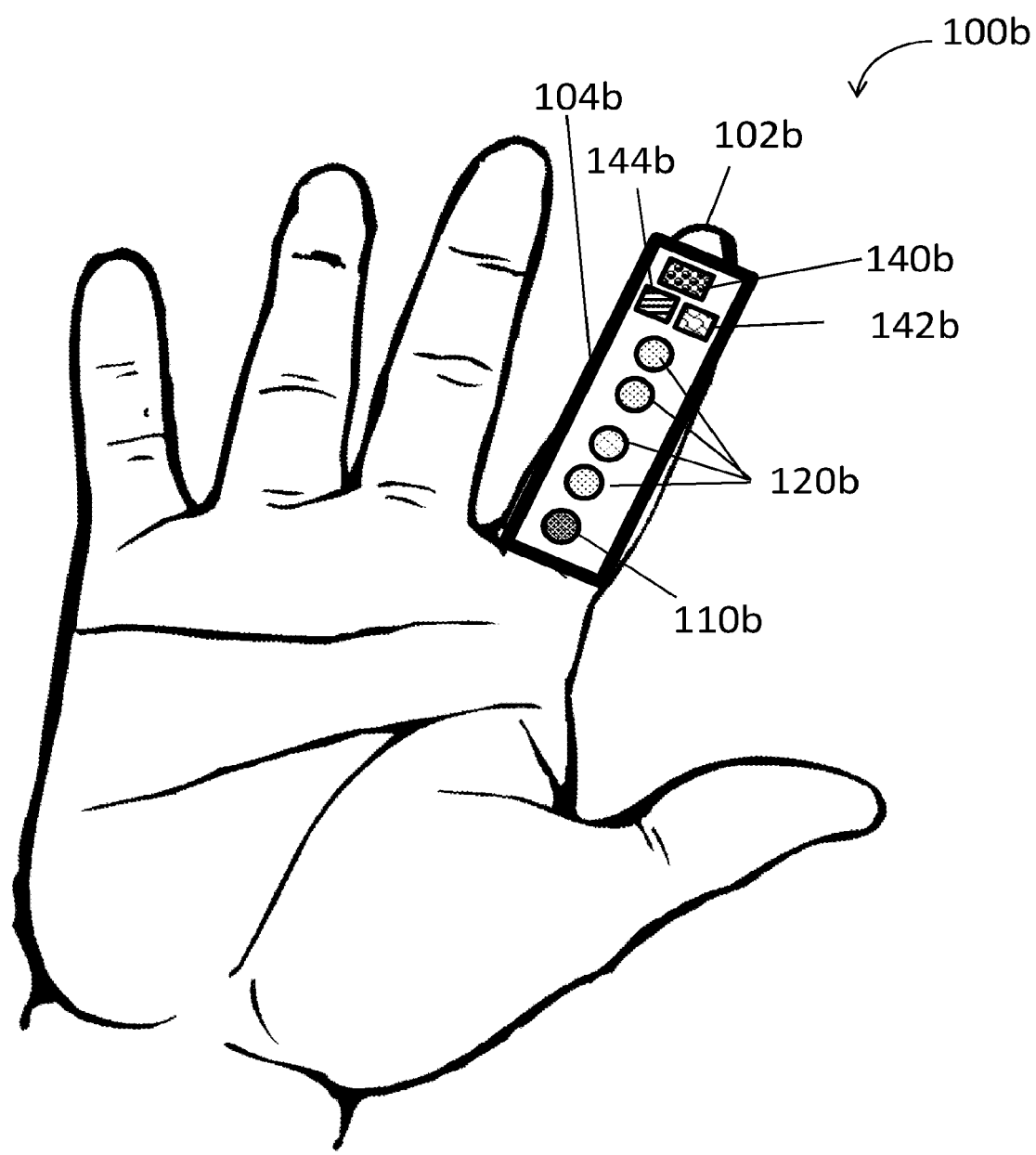
FIG. 1B schematically illustrates an array for monitoring physiological parameters attached along a length of a subject's finger, according to some embodiments.

Reference is now made to FIG. 1B, which schematically illustrates an array 100b for monitoring physiological parameters attached along a length of a subject's finger 102b, according to some embodiment. Array 100b includes a scaffold 104b, an active electrode 110b, a plurality of inactive electrodes 120b (here illustrated as 4 inactive electrodes), and additional sensors, here illustrated as a PPG sensor 140b, an accelerometer 142b and a temperature sensor 144b. Array 100b may further include at least one additional element, such as a resistor, a capacitor, a piezoelectric sensor, a thermistor, a solenoid diode or any combination thereof, as further described hereinbelow. It is understood to one of ordinary skill in the art that any of the electrodes on the array may serve as the active electrode, and the designation as an active electrode is based on the connection to a power/energy source only. It is further understood that the position of the active electrode as being closest to the hand palm is illustrative only and a different arrangement (for example, the active electrode being the distant most electrode) is likewise possible and thus falls within the scope of this disclosure. Similarly, the position of the additional sensors is for illustrative purpose only, and other positions along the array may also be envisaged. It is further understood that the electrodes face the finger of the subject and may not be visible when the array is attached to the finger.

Reference is now made to FIG. 2A-2F which schematically illustrate a front side (electrode exposing side) of a GSR electrode array 200a-200f with a scaffold 204, an active electrode 210 and a plurality of inactive electrodes 220 disposed along a longitudinal axis 250 thereof (illustrated in FIGS. 2A and 2B only), according to some embodiments. It is understood to one of ordinary skill in the art that any of the electrodes on the array may serve as the active electrode and the definition as an active electrode is based on the connection to a power/energy source only. It is further understood that the position of the active electrode as being closest to the hand palm is illustrative only and a different arrangement (for example, the active electrode being the distant most electrode) is likewise possible and thus falls within the scope of this disclosure. GSR electrode arrays 200a-200f optionally include a hydrogel compartment 230 in which each electrode is disposed. For simplicity, hydrogel compartment 230 is illustrated on a single electrode in FIG. 2A only, however it is understood that all the depicted electrodes in FIG. 2A to 2F may have similar hydrogel compartments. FIG. 2A to 2F depict non-limiting optional arrangements of active electrode 210 and inactive electrodes 220 on GSR electrode array 200a-200f. Specifically, FIG. 2A illustrates a GSR electrode array 200a in which active electrode 210 and the plurality of inactive electrodes 220 are positioned evenly along the length of longitudinal axis 250. FIG. 2B illustrates a GSR electrode array 200b in which active electrode 210 and inactive electrodes 220 are positioned along the length of longitudinal axis 250 but at different lateral positions. FIG. 2C illustrates a GSR electrode array 200c in which the distance d between each electrode and its neighboring electrodes is constant (d1=d2=d3=d4=d5). FIG. 2D illustrates a GSR electrode array 200d in which the distance d between each electrode and its neighboring electrodes is gradually increasing (d1<d2<d3<d4<d5). This configuration reduces the overall amount of electrodes while minimally influencing signal quality based on the assumption that the relative impact on a change in conductivity is larger when the distance between the active electrode and the inactive electrode is increased. FIG. 2E illustrates a GSR electrode array 200e in which the distance d between each electrode and its neighboring electrodes is gradually decreasing (d1>d2>d3>d4>d5). This configuration reduces the overall amount of electrodes while minimally influencing signal quality based on the assumption that signal quality is primarily a problem when skin dryness is high, in which case gradually reducing the distance to the active electrode may be desired. FIG. 2F illustrates a GSR electrode array 200f in which the distance d between each electrode and its neighboring electrodes is random (e.g. d1<d2>d3<d4>d5). This configuration reduces the overall amount of electrodes while optionally integrating the above-mentioned assumptions.

Figure 3:
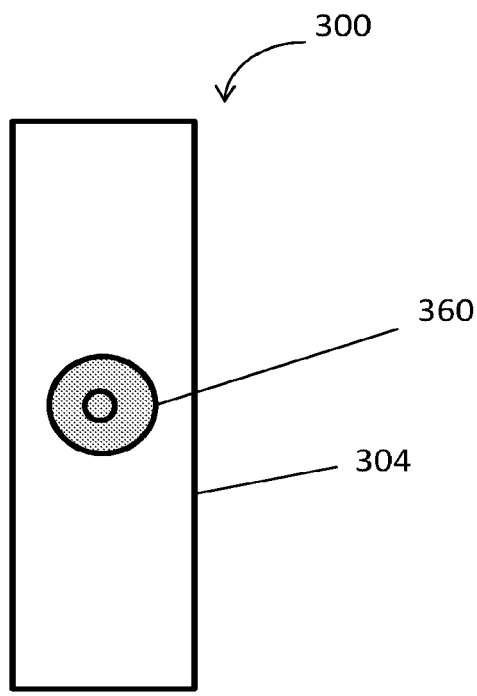
FIG. 3 schematically illustrates a back side of a GSR electrode array with a connection point disposed thereon, according to some embodiments.

Reference is now made to FIG. 3 which schematically illustrate a back side (connection side) of a GSR electrode array 300 with a connection point 360 disposed on a scaffold 304 thereof, according to some embodiment. Connection point 360 may be configured to receive an electrical signal (i.e. a voltage or a current) which is then supplied to the active electrode (such as active electrode 210 of FIG. 2A-2F). Connection point 360 may further be configured to transmit an electrical signal received from a measurement (such as any or all of inactive electrodes 220 of FIG. 2A to 2F) to a detection device (e.g. an ammeter—not shown). Connection point 360 may further be configured to transfer signals from additional elements on the array, such as, but not limited to, a humidity sensor, a PPG sensor or any other element incorporated onto the array.

Figure 4A:
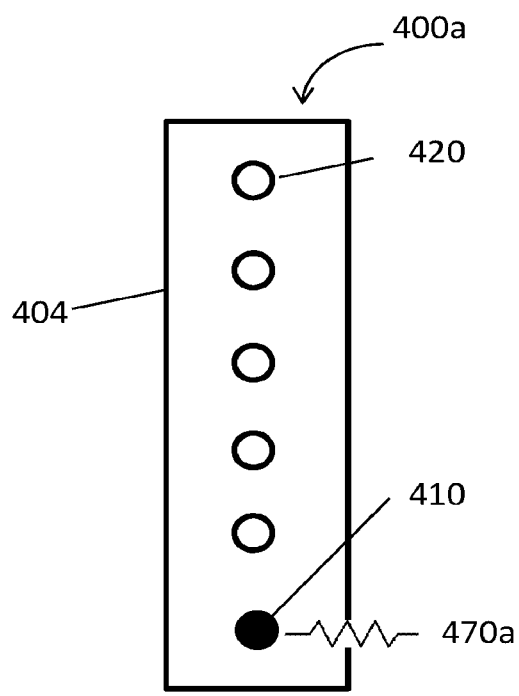
FIG. 4A schematically illustrates a GSR electrode array with an active electrode, a plurality of inactive electrodes and a resistor, according to some embodiments.
Figure 4B:
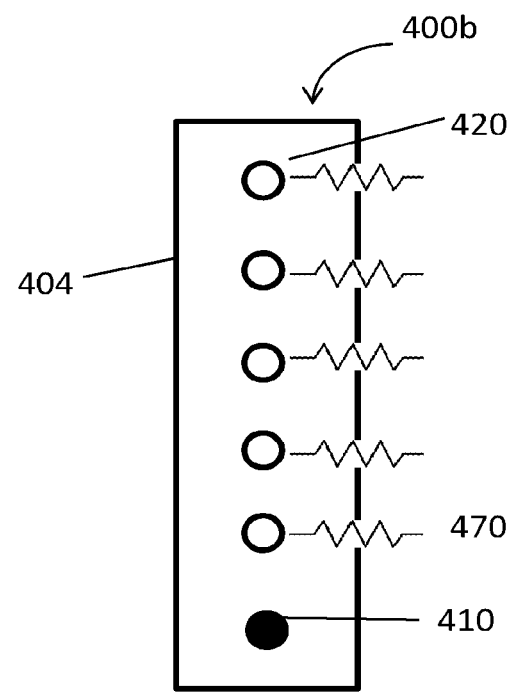
FIG. 4B schematically illustrates a GSR electrode array with an active electrode, a plurality of inactive electrodes and resistors, according to some embodiment.

Reference is now made to FIGS. 4A and 4B which schematically illustrate GSR electrode arrays 400a and 400b, respectively, each including a scaffold 404, an active electrode 410, a plurality of inactive electrodes, here illustrated as 4 inactive electrodes 420 and a resistor electrically connected to active electrode 410, such as resistor 470a in FIG. 4A or a resistor electrically connected to each of inactive electrodes 410 such as resistors 470b in FIG. 4B. Alternatively, the resistor may be part of a separate electrical circuit, which is not electrically connected to active electrode 410 or inactive electrodes 420 (option not shown). Resistors 470b may be of a same or different resistor value and may serve to harmonize the scale of measurements obtained from each of electrodes 420, as essentially described herein.

Figure 5:
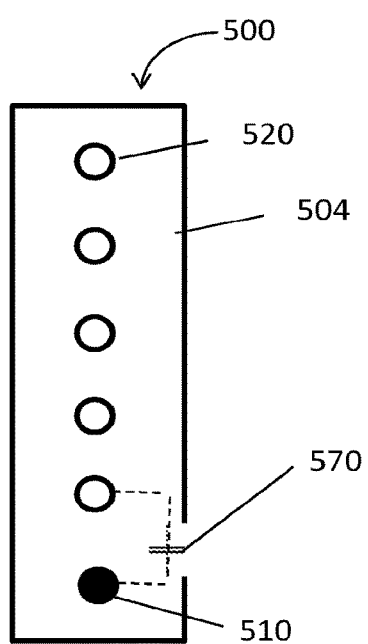
FIG. 5 schematically illustrates a GSR electrode array with an active electrode, a plurality of inactive electrodes and capacitors, according to some embodiments.

Reference is now made to FIG. 5 which schematically illustrates a GSR electrode array 500 with a scaffold 504, an active electrode 510, a plurality of inactive electrodes, here illustrated as 4 inactive electrodes 520, and capacitors 570 electrically connected between the active electrode and one of the plurality of inactive electrodes (for simplicity only a single capacitor, electrically connected between the active electrode and the first inactive electrode, is illustrated). It is understood that capacitors 570 may be of a different capacity value, thereby causing the time delay in the GSR measurement obtained from each of inactive electrodes 520 to be unique, as essentially discussed herein.

Figure 6:
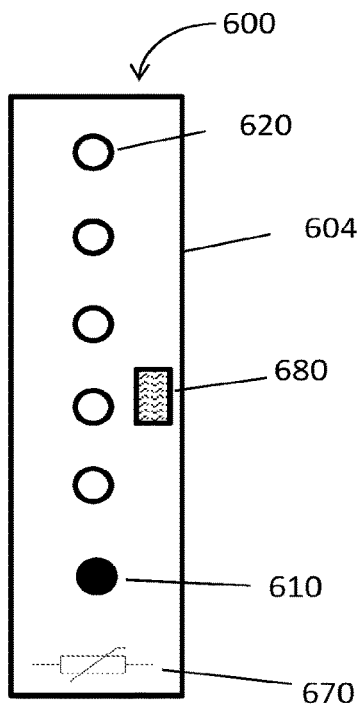
FIG. 6 schematically illustrates a GSR electrode array with an active electrode, a plurality of inactive electrodes and a thermistor, according to some embodiments.

Reference is now made to FIG. 6, which schematically illustrates a GSR electrode array 600 with a scaffold 604, an active electrode 610, a plurality of inactive electrodes, here illustrated as 4 inactive electrodes 620, and a thermistor 670. Incorporation of thermistor 670 into GSR array 600 may enable evening out of values obtained due to thermoregulation rather than physiological arousal (e.g. pain) by calibrating the GSR readings to the subject's body temperature. Thermistor 670 may further enable taking into consideration changes in blood volume, basal perspiration, room temperature, and/or environmental temperature, when determining a level of physiological arousal (e.g. pain). GSR electrode array 600 may optionally include a heat element 680 configured to heat the subject's finger when needed. According to some embodiments, thermistor 670 may provide an input indicator and/or a trigger activating the heat element 680. According to some embodiments, thermistor 670 may be part of a separate electrical circuit, which is not electrically connected to active electrode 610 or inactive electrodes 620. Alternatively, thermistor 670 (or a plurality of thermistors) may be electrically connected to active electrodes 610 or inactive electrodes 620 (option not shown). According to some embodiments, thermistor 670 may be electrically connected to heat element 680.

Figure 7:
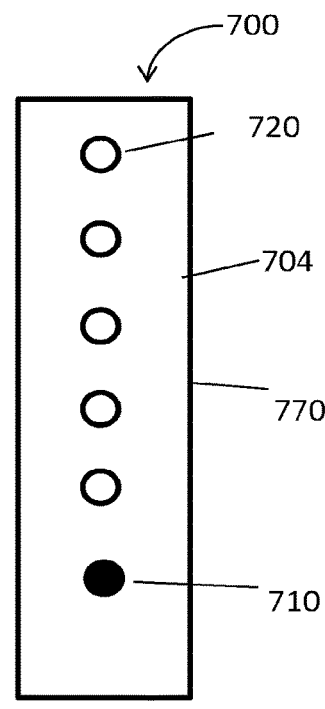
FIG. 7 schematically illustrates a GSR electrode array with an active electrode, a plurality of inactive electrodes and a piezoelectric sensor, according to some embodiments.

Reference is now made to FIG. 7, which schematically illustrates a GSR electrode array 700 with a scaffold 704, an active electrode 710, a plurality of inactive electrodes, here illustrated as 4 inactive electrodes 720, and a piezoelectric sensor 770. Piezoelectric sensor 770 may be so arranged as to enable determining whether the finger to which GSR electrode array 700 is attached is kept straight. This may ensure high quality monitoring, since a straight finger is imperative to the quality of the GSR measurements. According to some embodiments, the readings obtained from piezoelectric sensor 770 (optionally in combination with an additional piezoelectric sensor and/or PPG readings) may enable extraction of a pulse transient time (Ptt) of the subject's heart, as essentially described herein.

Figure 8:
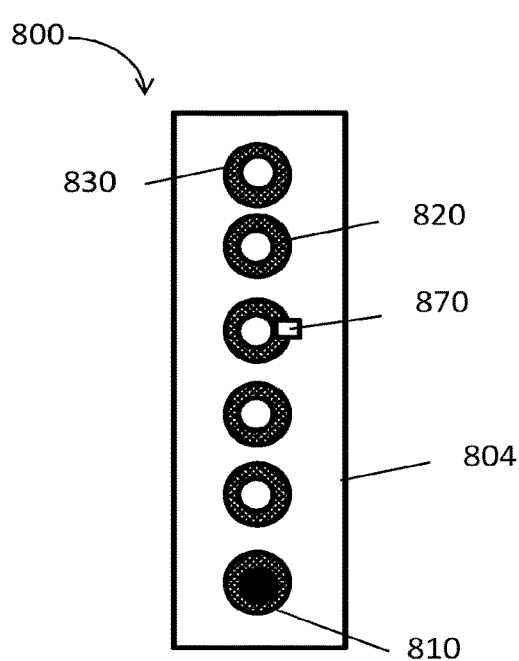
FIG. 8 schematically illustrates a GSR electrode array with an active electrode, a plurality of inactive electrodes and a humidity sensor, according to some embodiments.

Reference is now made to FIG. 8, which schematically illustrates a GSR electrode array 800 with a scaffold 804, an active electrode 810, a plurality of inactive electrodes 820, and a humidity sensor 870 (e.g. a humidity sensing electrical circuit as essentially described herein), according to some embodiments. Humidity sensor 870 may sense the humidity of a GSR electrode hydrogel in hydrogel compartment 830. According to some embodiments, humidity sensor 870 may sense the humidity of only one of hydrogel compartments 830. Alternatively, humidity sensor 870 may sense the humidity of all or some of hydrogel compartments 830. According to some embodiments, GSR electrode array 800 may include more than one humidity sensor, each sensor sensing the humidity of a different hydrogel compartment. Based on the determined humidity, humidity sensor 870 may provide a signal indicative of whether replacement of GSR array 800 is needed. Additionally or alternatively, humidity sensor 870 may provide a signal indicating that addition of hydrogel to hydrogel compartment 830 is required. According to this embodiment, GSR electrode array 800 may include an access point (not shown) enabling addition of hydrogel to hydrogel compartment 830.

Figure 9:
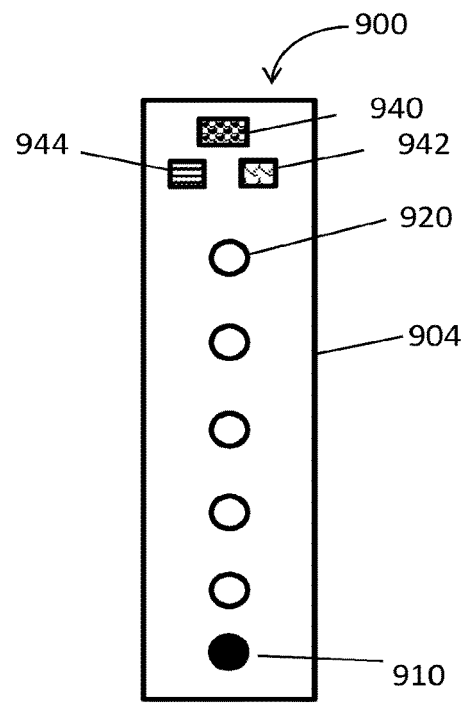
FIG. 9 schematically illustrates a GSR electrode array with an active electrode, a plurality of inactive electrodes, a PPG sensor, a temperature sensor and an accelerometer, according to some embodiments.

Reference is now made to FIG. 9, which schematically illustrates an array 900 for measuring a plurality of physiological signals. Array 900 includes a scaffold 904, an active electrode 910, a plurality of inactive electrodes, here illustrated as 4 inactive electrodes 920, and additional sensors of physiological parameters, here PPG sensor 940, accelerometer 942 and temperature sensor 944. Array 900 may thus form an integrative unit configured to obtain a plurality of physiological signals, all obtained from a single array, which preferably is attached to a single finger of a subject. Array 900 is thus configured to minimize noise resulting from obtaining physiological signals from different parts of a subject's body. Array 900 may further include at least one additional element, such as a resistor, a capacitor, a piezoelectric sensor, a thermistor, a solenoid diode, or any combination thereof, as essentially described herein.

Figure 10A:
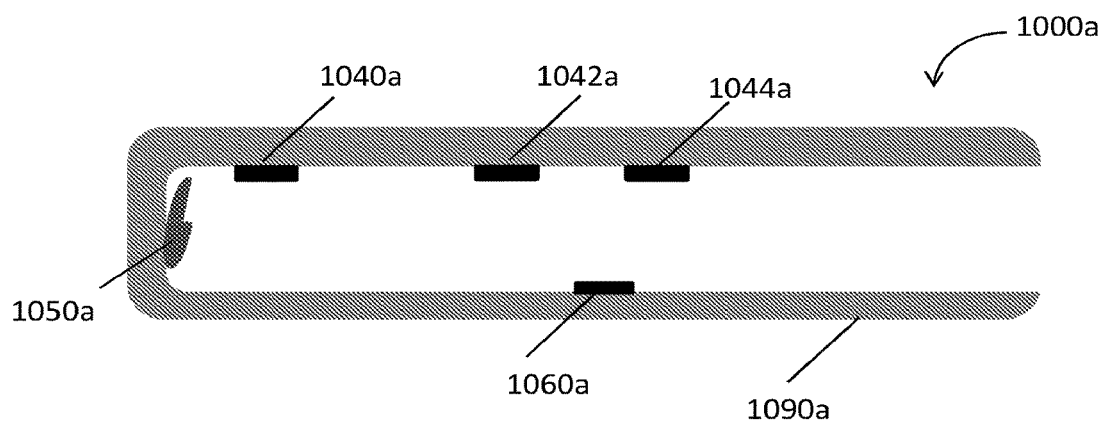
FIG. 10A schematically illustrates a perspective view of a finger probe, according to some embodiment.

Reference is now made to FIG. 10A, which schematically illustrates a perspective view of a finger probe 1000a, according to some embodiments. Finger probe 1000a includes a casing 1090a and at least one sensor configured to obtain a physiological signal, here a PPG sensor 1040a, an accelerometer 1042a and temperature sensor 1044a (location of sensors is arbitrary and serve an illustrative purpose only). Finger probe 1000a further includes a connection point 1060a configured for attachment of a GSR sensor, such as, but not limited to, any of the GSR arrays disclosed herein or combinations thereof. As a result, finger probe 1000a forms a single integrative unit configured for measurements of a plurality of physiological signals obtained from PPG sensor 1040a, accelerometer 1042a and temperature sensor 1044a and from a GSR electrode array when the latter is connected to connection point 1060a. Advantageously, the measurements obtained from all sensors (PPG sensor 1040a, accelerometer 1042a and temperature sensor 1044a and from a GSR electrode array) are measured from a single (and same) finger. Finger probe 1000a further includes a push button 1050a configured to close an open electrical circuit when a subject's finger is correctly positioned within finger probe 1000a. According to some embodiments, the open electrical circuit may be electrically connected to PPG sensor 1040a, accelerometer 1042a and temperature sensor 1044a in such manner that even when connected to a turned on power source (not shown), PPG sensor 1040a, accelerometer 1042a and temperature sensor 1044a remain shut off until a finger presses upon push button 1050a. According to some embodiments, the open electrical circuit may be electrically connected to a power supply such that power is provided to finger probe 1000a only when a finger presses upon push button 1050a. According to some embodiments, the open electrical circuit may be electrically connected to a medical device (not shown) configured to obtain measurements from PPG sensor 1040a, accelerometer 1042a, temperature sensor 1044a and from the GSR sensor connected to connection point 1060a of finger probe 1000a, such that the medical device will be turned on only when a finger presses upon push button 1050a. Additionally or alternatively, connection of a GSR electrode array (such as any of the GSR electrode arrays disclosed herein) to connection point 1060a, may serve as a trigger for activation of PPG sensor 1040a, accelerometer 1042a and temperature sensor 1044a. Additionally or alternatively, connection of a GSR electrode array (such as any of the GSR electrode arrays disclosed herein) to connection point 1060a, may serve as a trigger for activation of a power supply (not shown) configured to supply power to finger probe 1000a. Additionally or alternatively, connection of a GSR electrode array (such as any of the GSR electrode arrays disclosed herein) to connection point 1060a, may serve as a trigger for activation of a medical device (not shown) configured to obtain measurements from PPG sensor 1040a, accelerometer 1042a, temperature sensor 1044a and from a GSR sensor connected to finger probe 1000a. According to some embodiments, finger probe 1000a and/or PPG sensor 1040a, accelerometer 1042a and temperature sensor 1044a incorporated therein may provide measurements only when a GSR sensor (e.g. any of the GSR electrode arrays disclosed herein) is attached to connection point 1060a. This may ensure that monitoring is only performed when a GSR sensor is connected to finger probe 1000a.

Figure 10B:
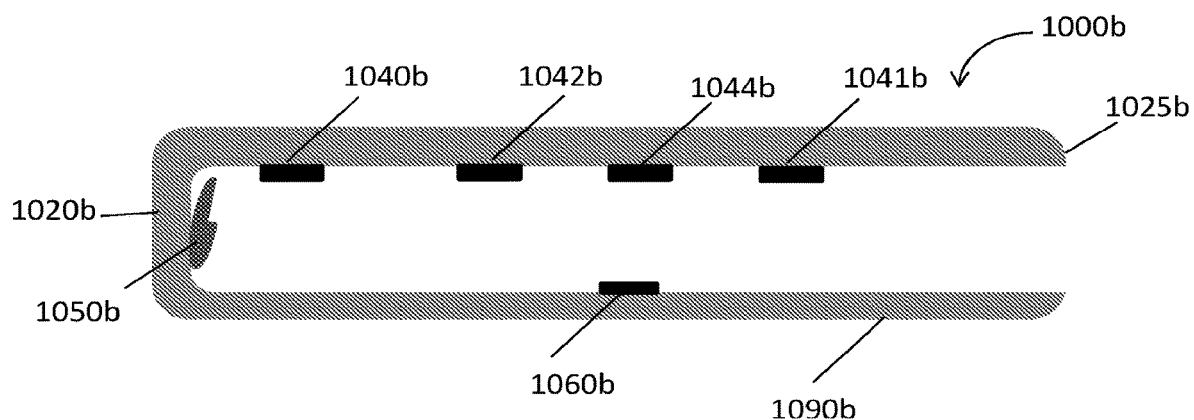
FIG. 10B schematically illustrates a perspective view of a finger probe, according to some embodiment.

Reference is now made to FIG. 10B, which schematically illustrates a perspective view of a finger probe 1000b, according to some embodiments. Finger probe 1000b includes a casing 1090b and two PPG sensors 1040b and 1041b, an accelerometer 1042b and temperature sensor 1044b. PPG sensor 1040b is positioned in proximity to a distal end 1020b of finger probe 1000b whereas PPG sensor 1041b is positioned in proximity to a proximal end 1025b of finger probe 1000b. The relative position of PPG sensors 1040b and 1041b facilitates obtaining signals from a same arteriole, but spaced apart along a subjects finger (i.e. at the bottom of the finger and at the tip of the finger), when the finger is inserted into finger probe 100b, thereby facilitating extraction of Ptt readings, as essentially described herein. The relative position of accelerometer 1042b and temperature sensor 1044b is arbitrary and serve an illustrative purpose only. Finger probe 1000b further includes a connection point 1060b configured for attachment of a GSR sensor, such as, but not limited to, any of the GSR arrays disclosed herein or combinations thereof. As a result, finger probe 1000b forms a single integrative unit configured for measurements of a plurality of physiological signals obtained from PPG sensors 1040b and 1041b, accelerometer 1042b and temperature sensor 1044b and from a GSR electrode array, when the latter is connected to connection point 1060b. Advantageously, the measurements obtained from all sensors (PPG sensors 1040b and 1041b, accelerometer 1042b and temperature sensor 1044b and from a GSR electrode array) are measured from a single (and same) finger. Finger probe 1000b further includes a push button 1050b configured to close an open electrical circuit when a subject's finger is correctly positioned within finger probe 1000b. According to some embodiments, the open electrical circuit may be electrically connected to PPG sensors 1040b and 1041b, accelerometer 1042b and temperature sensor 1044b in such manner that even when connected to a turned on power source (not shown), PPG sensors 1040b and 1041b, accelerometer 1042b and temperature sensor 1044b remain shut off until a finger presses upon push button 1050b. According to some embodiments, the open electrical circuit may be electrically connected to a power supply such that power is provided to finger probe 1000b only when a finger presses upon push button 1050b. According to some embodiments, the open electrical circuit may be electrically connected to a medical device (not shown) configured to obtain measurements from PPG sensors 1040b and 1041b, accelerometer 1042b, temperature sensor 1044b and from the GSR sensor connected to connection point 1060b of finger probe 1000b, such that the medical device will be turned on only when a finger presses upon push button 1050b. Additionally or alternatively, connection of a GSR electrode array (such as any of the GSR electrode arrays disclosed herein) to connection point 1060b, may serve as a trigger for activation of PPG sensors 1040b and 1041b, accelerometer 1042b and temperature sensor 1044b. Additionally or alternatively, connection of a GSR electrode array (such as any of the GSR electrode arrays disclosed herein) to connection point 1060b, may serve as a trigger for activation of a power supply (not shown) configured to supply power to finger probe 1000b. Additionally or alternatively, connection of a GSR electrode array (such as any of the GSR electrode arrays disclosed herein) to connection point 1060b, may serve as a trigger for activation of a medical device (not shown) configured to obtain measurements from PPG sensors 1040b and 1041b, accelerometer 1042b, temperature sensor 1044b and from a GSR sensor connected to finger probe 1000b. According to some embodiments, finger probe 1000b and/or PPG sensors 1040b and 1041b, accelerometer 1042b and temperature sensor 1044b incorporated therein may provide measurements only when a GSR sensor (e.g. any of the GSR electrode arrays disclosed herein) is attached to connection point 1060b. This may ensure that monitoring is only performed when a GSR sensor is connected to finger probe 1000b.

Figure 10C:
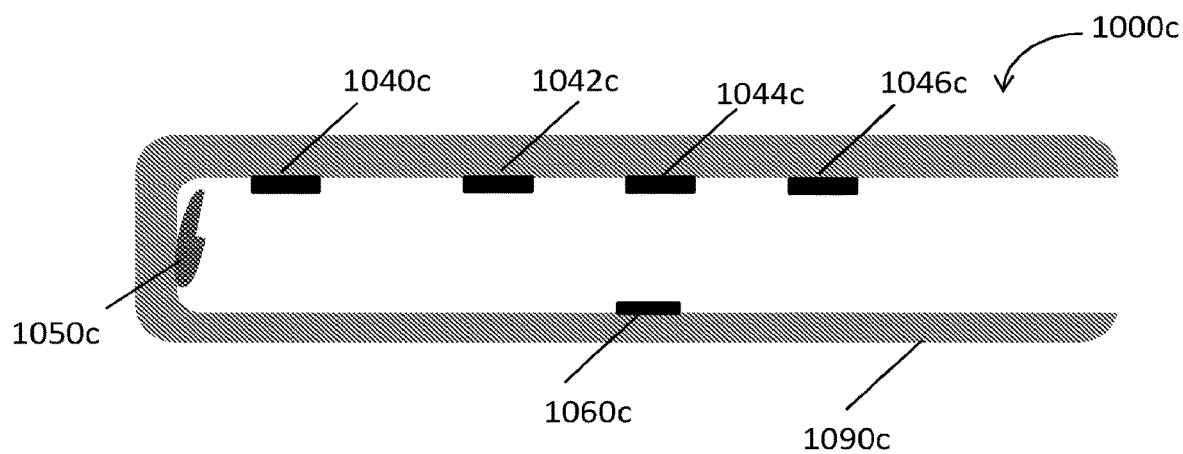
FIG. 10C schematically illustrates a perspective view of a finger probe, according to some embodiment.

Reference is now made to FIG. 10C, which schematically illustrates a perspective view of a finger probe 1000c, according to some embodiments. Finger probe 1000c includes a casing 1090c and a PPG sensor 1040c, an accelerometer 1042c, a temperature sensor 1044c and a piezoelectric sensor 1046c. Signals obtained from PPG sensor 1040c and piezoelectric sensor 1046c facilitate extraction of Ptt readings, as essentially described herein. Finger probe 1000c further includes a connection point 1060c configured for attachment of a GSR sensor, such as, but not limited to, any of the GSR arrays disclosed herein or combinations thereof. As a result, finger probe 1000c forms a single integrative unit configured for measurements of a plurality of physiological signals obtained from PPG sensor 1040c, accelerometer 1042c, temperature sensor 1044c, piezoelectric sensor 1046c and from a GSR electrode array, when the latter is connected to connection point 1060c. Advantageously, the measurements obtained from all sensors (PPG sensor 1040c, accelerometer 1042c, temperature sensor 1044c, piezoelectric sensor 1046c and the GSR electrode array) are measured from a single (and same) finger. Finger probe 1000c further includes a push button 1050c configured to close an open electrical circuit when a subject's finger is correctly positioned within finger probe 1000c. According to some embodiments, the open electrical circuit may be electrically connected to PPG sensor 1040c, accelerometer 1042c, temperature sensor 1044c and/or piezoelectric sensor 1046c in such manner that even when connected to a turned on power source (not shown), PPG sensor 1040c, accelerometer 1042c, temperature sensor 1044c and/or piezoelectric sensor 1046c remain shut off until a finger presses upon push button 1050c. According to some embodiments, the open electrical circuit may be electrically connected to a power supply such that power is provided to finger probe 1000c only when a finger presses upon push button 1050c. According to some embodiments, the open electrical circuit may be electrically connected to a medical device (not shown) configured to obtain measurements from PPG sensor 1040c, accelerometer 1042c, temperature sensor 1044c and/or piezoelectric sensor 1046c and from the GSR sensor connected to connection point 1060c of finger probe 1000c, such that the medical device will be turned on only when a finger presses upon push button 1050c. Additionally or alternatively, connection of a GSR electrode array (such as any of the GSR electrode arrays disclosed herein) to connection point 1060c, may serve as a trigger for activation of PPG sensor 1040c, accelerometer 1042c, temperature sensor 1044c and/or piezoelectric sensor 1046c. Additionally or alternatively, connection of a GSR electrode array (such as any of the GSR electrode arrays disclosed herein) to connection point 1060c, may serve as a trigger for activation of a power supply (not shown) configured to supply power to finger probe 1000c. Additionally or alternatively, connection of a GSR electrode array (such as any of the GSR electrode arrays disclosed herein) to connection point 1060c, may serve as a trigger for activation of a medical device (not shown) configured to obtain measurements from PPG sensor 1040c, accelerometer 1042c, temperature sensor 1044c and/or piezoelectric sensor 1046c and from a GSR sensor connected to finger probe 1000c. According to some embodiments, finger probe 1000c and/or PPG sensor 1040c, accelerometer 1042c, temperature sensor 1044c and piezoelectric sensor 1046c incorporated therein may provide measurements only when a GSR sensor (e.g. any of the GSR electrode arrays disclosed herein) is attached to connection point 1060c. This may ensure that monitoring is only performed when a GSR sensor is connected to finger probe 1000c.

Figure 11:
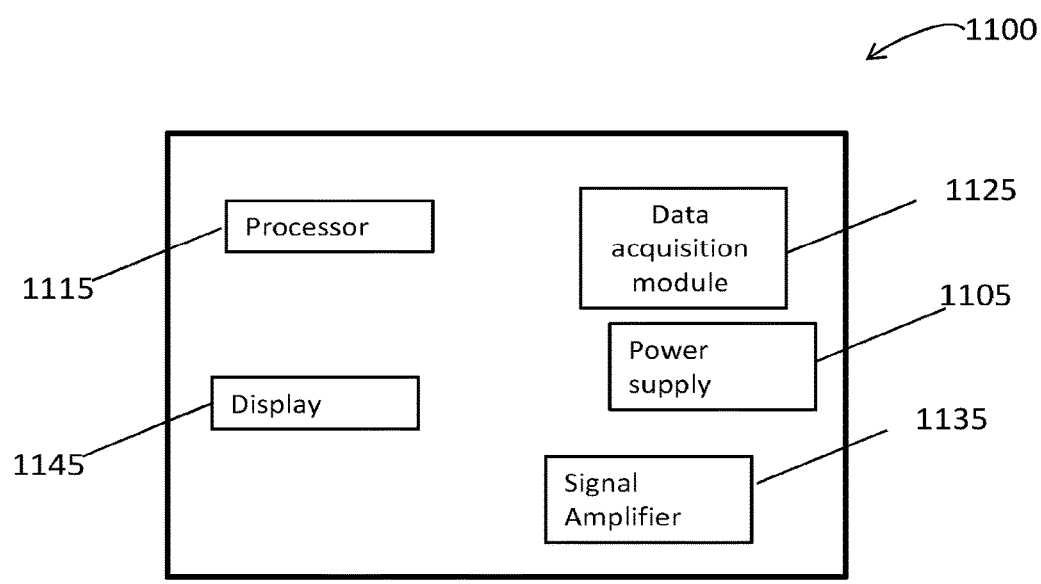
FIG. 11 schematically illustrates a medical device configured to utilize a GSR electrode array, according to some embodiments.

Reference is now made to FIG. 11, which schematically illustrates a medical device 1100 configured to utilize a GSR electrode array, such as any of the GSR electrode arrays disclosed herein. Medical device 1100 includes a power supply 1105. Power supply 1105 may be configured to provide a voltage to an active electrode of a GSR sensor. Additionally or alternatively, power supply 1105 may be configured to supply power to the physiological sensors of a finger probe, such as PPG sensor 1040, accelerometer 1042 and temperature sensor 1044 of finger probe 1000, described hereinabove. Medical device 1100 further includes a data acquisition module 1125 configured to receive signals from an array (such as any of the arrays described herein or from a finger probe including same); and a signal amplifier 1135 configured to amplify the signal, such as, for example, signals obtained from a GSR array. Medical device 1100 further includes a processor 1115 configured to determine a preferred inactive electrode among a plurality of inactive electrodes on the GSR electrode array, based on the received electrical signal, and to determine the electrical conductance of the subject's skin based on an integrated analysis of an electrical signal received from the preferred inactive electrode and on a distance between the active electrode and the preferred inactive electrode. According to some embodiments, processor 1115 may be configured to determine changes in the electrical conductance of the subject's skin based on changes in the electrical signal obtained during subsequent measurements and based on the distance between the active electrode and the preferred electrode. Medical device 1100 may further include a display 1145 configured to display the determined conductance of the subject's skin and/or the physiological arousal (e.g. pain level) determined based at least partially on the determined skin conductance.

Figure 12:
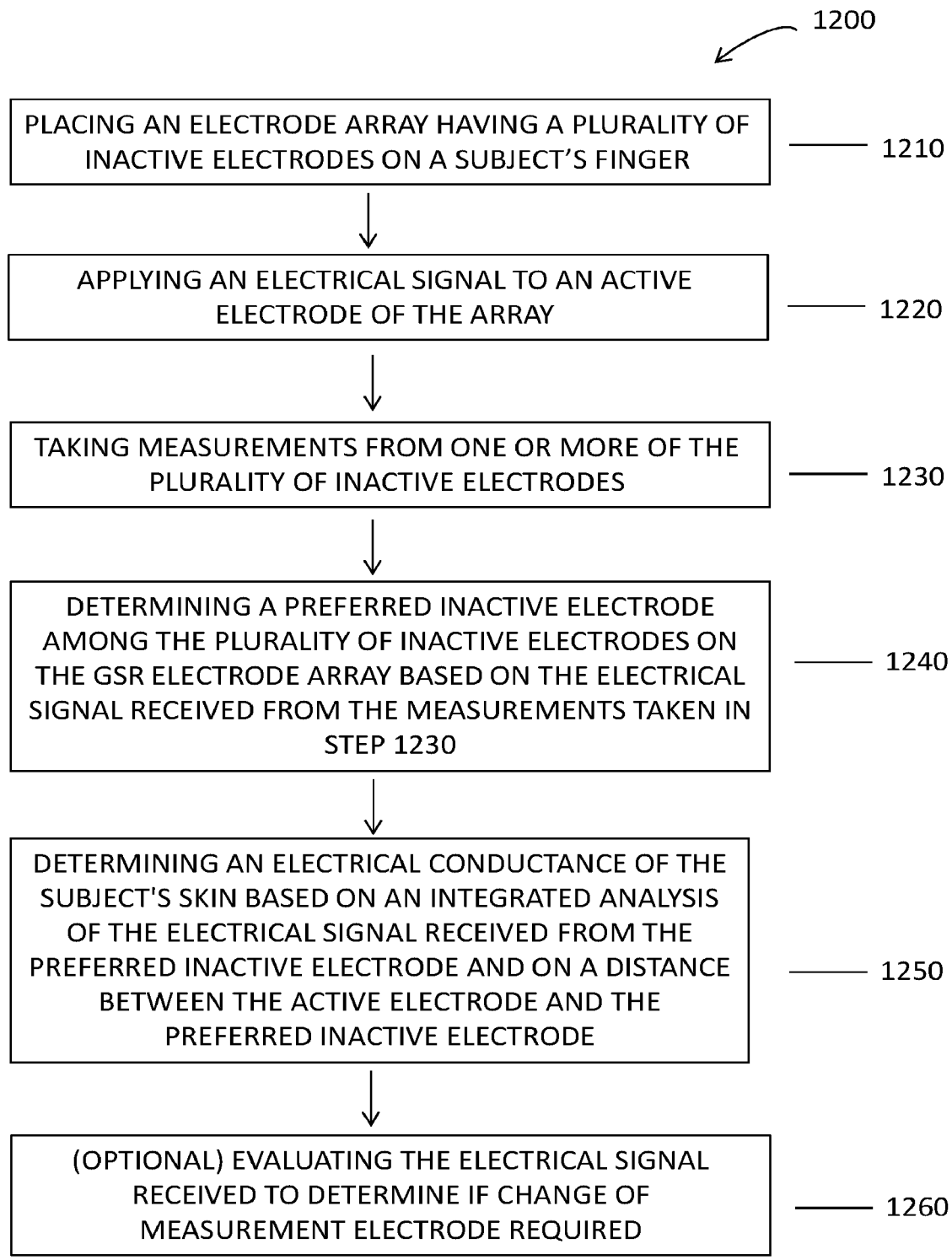
FIG. 12 is an illustrative flowchart of a method for utilizing a GSR electrode array, according to some embodiments.

Reference is now made to FIG. 12, which is an illustrative flowchart 1200 of a method for utilizing a GSR electrode array, according to some embodiment. It is understood by one of ordinary skill of the art that the order of the methods as described should not be construed as sequential steps, and a different sequence of events may be envisaged.

In step 1210 an array, such as the GSR array described herein or a probe containing same, is placed on a subject's finger. In step 1220, an electrical signal (voltage or current) is applied to an active electrode. In step 1230, a measurement is taken from one or more of a plurality of inactive electrodes. In step 1240, a preferred inactive electrode is determined among a plurality of inactive electrodes on the GSR electrode array, based on the measurement taken in step 1230. In case the signal obtained is too low, the measurement may be taken from a closer inactive electrode. In case the signal is saturated, the measurement may be taken from a further distanced inactive electrode. According to some embodiments, determination of a preferred electrode may be based on simultaneous or sequential measurements obtained from all of the plurality of inactive electrodes, for example, by electing the electrode with the best signal. According to some embodiments, determination of a preferred electrode may be based on a signal obtained from a predetermined first inactive electrode e.g. the center most inactive electrode. The preferred electrode may then be determined to be an inactive electrode closer to the active electrode, an inactive electrode further distanced from the active electrode or the initially chosen inactive electrode. According to some embodiments, determination of a preferred electrode may be based on a preferred distance between the active electrode and the inactive electrode calculated based on the signal obtained from a predetermined initially chosen inactive electrode. Once a preferred inactive electrode has been determined in step 1240, the electrical conductance of the subject's skin may be determined, in step 1250, based on an integrated analysis of an electrical signal received from the preferred inactive electrode and on a distance between the active electrode and the preferred inactive electrode. Optionally, in step 1260, the signal obtained may be continuously evaluated by taking into consideration changes in additional factors, such as, but not limited to, environment temperature. It is understood that changes in, for example, the environment temperature may cause a change in the determination of an optimal inactive electrode. Such temperature change may influence the basal level of the sweating, not as a result from response to pain, but as a response to environmental changes and/or temperature regulation of the body, which may, as well, influence other physiological parameters measured by the different sensors that may be included as depicted in FIG. 9.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. Unless otherwise defined, all technical and scientific terms used herein have the same meaning as commonly understood by one of ordinary skill in the art to which this invention belongs.

Unless specifically stated otherwise, as apparent from the following discussions, it is appreciated that throughout the specification discussions utilizing terms such as "processing", "computing", "calculating", "determining", "estimating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, magnetic-optical disks, read-only memories (ROMs), random access memories (RAMs), electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

The invention may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A galvanic skin response (GSR) electrode array comprising:
 a scaffold configured for attachment along a length of a subject's finger, the scaffold comprising:
  an active electrode configured to provide an electrical signal to at least two measurement electrodes,
  wherein the active electrode is an electrode configured to continuously receive an applied electrical signal,
  at least two measurement electrodes, each configured to simultaneously collect the electrical signal transferred from the active electrode along the subject's skin,
  wherein each of the at least two measurement electrodes configured to be positioned at a different predetermined distance from the active electrode based on attachment along the length of the subject's finger;
  wherein each of the at two measurement electrodes is configured to produce a signal indicative of the strength of the electrical signal collected, and
  wherein the strength of the electrical signal collected by each of the at least two measurement electrodes depends on the conductivity of the subject's skin and the distance between each of the at least two measurement electrodes and the active electrode.

2. The GSR electrode array of claim 1, further comprising a connection point enabling transmittal of the electrical signal collected by each of the at least two measurement electrodes.

3. The GSR electrode array of claim 1, wherein the active electrode comprises a hydrogel configured to mediate contact between the active electrode and the subject's skin and wherein each of the at least two measurement electrodes comprise a hydrogel configured to mediate contact between the measurement electrode and the subject's skin.

4. The GSR electrode array of claim 3, further comprising a humidity sensor configured to sense the humidity of the hydrogel.

5. The GSR electrode array of claim 1, wherein a distance between the active electrode and a first of the at least two measurement electrodes is different than a distance between the first electrode and a second of the at least two measurement electrodes.

6. The GSR electrode array of claim 1, wherein the at least two measurement electrodes are identical.

7. The GSR electrode array of claim 1, wherein the at least two measurement electrodes are made from a different material.

8. The GSR electrode array of claim 1, wherein the at least two measurement electrodes have a different size and/or shape.

9. The GSR electrode array of claim 1, further comprising at least one heating element configured to heat the subject's finger.

10. The GSR array of claim 1, further comprising at least one sensor selected from the group consisting of a PPG sensor, an accelerometer, a temperature sensor, a diffused correlation spectroscopy (DCS) sensor, an acoustics sensor, a bio-impedance sensor, a piezoelectric sensor and any combination thereof.

11. The GSR array of claim 1, further comprising a pocket and at least one strap which, when pulled, is configured to generate a vacuum in the pocket, thereby sucking in a skin of the subject in contact with the pocket.

12. A method for determining electrical conductance of a subject's skin, the method comprising:
 receiving electrical signals from the measurement electrodes of a GSR electrode array of claim 1,
 determining a preferred measurement electrode among the plurality of measurement electrodes based on the received electrical signal; and
 determining the electrical conductance of the subject's skin based on an integrated analysis of an electrical signal received from the preferred measurement electrode and on a distance between the active electrode and the preferred measurement electrode.

13. The method of claim 12, wherein the electrical conductance of the subject's skin comprises providing a weight factor to the received electrical signal, wherein the weight factor is based on a distance between the active electrode and the measurement electrode determined as producing an optimal signal.

14. The method of claim 12, further comprising measuring a change in the electrical conductance of the subject's skin based on a change in an electrical signal obtained during a first measurement and a second measurement of the signal obtained from the measurement electrode determined as producing an optimal signal.

15. A method for determining a value of a physiological parameter, the method comprising:
    applying an alternative current (AC) excitation at a changing frequency to an active electrode;
    measuring a first electrical signal obtained from a first measurement electrode of the GSR electrode array of claim 1 after a first predetermined time;
    measuring a second electrical signal obtained from a second measurement electrode after a second predetermined time; and
    determining the value of the physiological parameter based on the first electrical signal and the second electrical signal.

16. The method of claim 15, wherein the physiological parameter is a hemodynamic parameter selected from blood flow, heart rate, pulse transient time (PTT) and any combination thereof.

17. The method of claim 15, wherein the physiological parameter is a respiration parameter selected from the group consisting of: a respiration rate, apnea, fast/slow changes in the respiration, and any combination thereof.

18. The method of claim 15, wherein determining the value of the physiological parameter further comprises obtaining at least one signal from: a PPG sensor, a piezoelectric sensor, a diffused correlation spectroscopy (DCS) sensor, an acoustics sensor, a bio-impedance sensor, a temperature sensor, or any combination thereof.

19. A finger probe, comprising:
    at least one sensor selected from the group consisting of: a photoplethysmograph (PPG) sensor, an accelerometer, a temperature sensor, a diffused correlation spectroscopy (DCS) sensor, an acoustics sensor, a bio-impedance sensor, a piezoelectric sensor, and any combination thereof; and
    a connection point connectable to the GSR electrode array of claim 1.

20. The finger probe of claim 19, wherein when the SGR electrode array is electrically connected to the connection point, the at least one sensor is activated.

21. The finger probe of 43, comprising at least two sensors.

22. The finger probe of claim 21 wherein n the at least two sensors comprise a PPG sensor, a piezoelectric sensor, or any combination thereof.

23. The finger probe of claim 22, wherein a first of the at least two sensors is positioned at a proximal end of the finger probe and a second of the at least two sensors is positioned at a distal end of the finger probe.

24. The finger probe of 43, further comprising a humidity sensor configured to sense a humidity of a hydrogel.

* * * * *